(12) United States Patent
Coudane et al.

(10) Patent No.: US 9,737,621 B2
(45) Date of Patent: Aug. 22, 2017

(54) MRI-VISIBLE HYDROPHOBIC COPOLYMER

(71) Applicant: Centre National de la Recherche Scientifique, Paris (FR)

(72) Inventors: Jean Coudane, Lattes (FR); Vincent Darcos, Viols le Fort (FR); Sarah El Habnouni, Vergeze (FR); Xavier Garric, Montpellier (FR); Laurent Lemaire, Beaucouze (FR); Benjamin Nottelet, Montpellier (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/364,007

(22) PCT Filed: Dec. 7, 2012

(86) PCT No.: PCT/IB2012/057074
§ 371 (c)(1),
(2) Date: Jun. 9, 2014

(87) PCT Pub. No.: WO2013/084204
PCT Pub. Date: Jun. 13, 2013

(65) Prior Publication Data
US 2014/0302324 A1 Oct. 9, 2014

(30) Foreign Application Priority Data
Dec. 9, 2011 (FR) ...................................... 11 61436

(51) Int. Cl.
| | | |
|---|---|---|
| A61K 49/12 | (2006.01) | |
| A61L 29/08 | (2006.01) | |
| A61L 27/14 | (2006.01) | |
| A61L 27/34 | (2006.01) | |
| A61L 27/50 | (2006.01) | |
| A61L 29/04 | (2006.01) | |
| A61L 29/18 | (2006.01) | |
| A61L 31/04 | (2006.01) | |
| A61L 31/10 | (2006.01) | |
| A61L 31/18 | (2006.01) | |

(52) U.S. Cl.
CPC .......... *A61K 49/126* (2013.01); *A61K 49/128* (2013.01); *A61L 27/14* (2013.01); *A61L 27/34* (2013.01); *A61L 27/50* (2013.01); *A61L 29/04* (2013.01); *A61L 29/085* (2013.01); *A61L 29/18* (2013.01); *A61L 31/04* (2013.01); *A61L 31/10* (2013.01); *A61L 31/18* (2013.01); *Y10T 428/2982* (2015.01)

(58) Field of Classification Search
CPC ..... A61K 49/126; A61K 49/128; A61L 31/04; A61L 31/10; A61L 31/18; A61L 29/04; A61L 29/085; A61L 29/18; A61L 27/14; A61L 27/34; A61L 27/50; Y10T 428/2982
See application file for complete search history.

(56) References Cited

U.S. PATENT DOCUMENTS

| | | |
|---|---|---|
| 4,822,594 A | 4/1989 | Gibby |
| 6,361,759 B1 | 3/2002 | Frayne et al. |
| 2002/0176822 A1 | 11/2002 | Frayne et al. |
| 2004/0081604 A1 | 4/2004 | Lemaire et al. |
| 2007/0202047 A1 | 8/2007 | Wolf et al. |
| 2008/0073272 A1 | 3/2008 | Lemaire et al. |
| 2012/0178872 A1 | 7/2012 | Blanquer et al. |

FOREIGN PATENT DOCUMENTS

| | | |
|---|---|---|
| JP | 2000-507962 | 6/2000 |
| WO | WO 99/60920 A2 | 12/1999 |
| WO | WO 03/045457 A2 | 6/2003 |
| WO | WO 2008/034911 A1 | 3/2008 |
| WO | WO 2011/004332 A1 | 1/2011 |

OTHER PUBLICATIONS

Blanquer, S., et al.; Journal of Polymer Science: Part A: Polymer Chemistry, 2010, p. 5891-5898.*
Riva, R., et al.; Macromolecules, 2007, p. 796-803.*
Vanasschen, C., et al.; Inorganic Chemistry, 2011, p. 8946-8958.*
Irma Perez-Baena, et al., "Single-chain polyacrylic nanoparticles with multiple Gd(III) centres as potential MRI contrast agents", Journal of Materials Chemistry, vol. 20, (2010), pp. 6916-6922.
Li, et al., "Amphiphilic multiarm star block copolymer-based multifunctional unimolecular micelles for cancer targeted drug delivery and MR imaging", Biomaterials, Elsevier, vol. 32, No. 27, XP028100850, May 2011, pp. 6595-6605.
Zhang, et al., Fabrication of Polymer-Gadolinium (III) Complex Nanomicelle from Poly (ethylene glycol)-Polysuccinimide Conjugate and Diethylenetriaminetetraacetic Acid-Gadolinium as Magnetic Resonance Imaging Contrast Agents, Journal of Applied Polymer Science, vol. 120, No. 5, XP002677250, Jun. 2011, pp. 2596-2605.
Pressly, et al., "Structural Effects on the Biodistribution and Positron Emission Tomography (PET) Imaging of Well-Defined $^{64}$Cu-Labeled Nanoparticles Comprised of Amphiphilic Block Graft Copolymers)", Biomacromolecules, vol. 8, No. 10, XP002677253, Oct. 2007, pp. 3126-3134.

(Continued)

*Primary Examiner* — Robert Jones, Jr.
(74) *Attorney, Agent, or Firm* — Oblon, McClelland, Maier & Neustadt, L.L.P.

(57) ABSTRACT

The invention relates to a hydrophobic thermoplastic copolymer which is in particular of use for manufacturing and/or coating medical devices, in particular implantable medical devices, characterized in that it is obtained by copolymerization, and in that it comprises at least one first monomer unit and at least one second monomer unit onto which is grafted a paramagnetic-ion-chelating ligand which can complex with such a paramagnetic ion or a paramagnetic-ion-chelating ligand which is complexed with such a paramagnetic ion, wherein the second monomer unit is grafted in sufficient amount for the copolymer to be visible in magnetic resonance imaging when it is complexed with said paramagnetic ion. The invention also relates to a method for obtaining said hydrophobic thermoplastic copolymer.

12 Claims, 4 Drawing Sheets

(56) References Cited

OTHER PUBLICATIONS

Lee, et al., "Diethylenetriaminepentaacetic Acid-Gadolinium (DTPA-Gd)-Conjugated Polysuccinimide Derivatives as Magnetic Resonance Imaging Contrast Agents", Bioconjugate Chemistry, vol. 17, No. 3, XP002677252, May 2006, pp. 700-706.

Zhang, et al., "Micelles Based on Biodegradable Poly(L-glutamic acid)-b-Polylactide with Paramagnetic Gd Ions Chelated to the Shell Layer as a Potential Nanoscale MRI-Visible Delivery System", Biomacromolecules, vol. 9, No. 1, XP002600870, Jan. 2008, pp. 36-42.

Kurita, et al., "Gd-DTPA-based MR-visible Polymer for Direct Visualization of Interventional Devices", Magnetic Resonance in Medical Sciences, vol. 10, No. 4, XP002677251, Dec. 2011, pp. 263-267.

Pillai, et al., "New cross-linking quinoline and quinolone based luminescent lanthanide probes for sensitive labeling", Proceedings of SPIE, vol. 8233, XP002677254, 2012, 12 pages.

International Search Report dated Mar. 19, 2013, in PCT/IB12/057074 filed Dec. 7, 2012.

French Preliminary Search Report dated Jun. 7, 2012, in French Application No. 1161436 filed Dec. 9, 2011.

Written Opinion (English machine translation) of the International Searching Authority dated Mar. 19, 2013, in PCT/IB12/057074 filed Dec. 7, 2012.

Written Opinion (English machine translation) of the International Searching Authority dated Jun. 7, 2012, in French Application No. 1161436 filed Dec. 9, 2011.

Sieving, P.F., et al., "Preparation and Characterization of Paramagnetic Polychelates and Their Protein Conjugates," Bioconjugate Chemistry, vol. 1, XP002600871, 1989, pp. 65-71.

Rebizak, R., "Polymeric Conjugates of $Gd^{3+}$-Diethylenetriaminepentaacetic Acid and Dextran. 2. Influence of Spacer Arm Length and Conjugate Molecular Mass on the Paramagnetic Properties and Some Biological Parameters," Bioconjugate Chemistry, vol. 9, XP002600872, 1998, pp. 94-99.

Ponsart, S., et al., "A Novel Route to Poly(E-carprolactone)-Based Copolymers via Anionic Derivatization," Biomacromolecules, vol. 1, 2000, pp. 275-281.

International Search Report dated Sep. 29, 2010 in PCT/IB10/53111 Filed Jul. 7, 2010.

Office Action as received in the corresponding Japanese Patent Application No. 2014-545443 dated Mar. 10, 2017 w/English translation.

* cited by examiner

MRI-VISIBLE HYDROPHOBIC COPOLYMER

The present invention relates to the field of medical devices, notably implantable, visible in magnetic resonance imaging.

The present invention relates more particularly to a new thermoplastic copolymer, having the property of being hydrophobic and insoluble in biological fluids, useful for manufacturing and/or coating medical devices, notably implantable, visible temporarily or permanently in magnetic resonance imaging.

The invention further relates to a method of preparing such a copolymer and a method of preparing a medical device, notably implantable, detectable in magnetic resonance imaging, comprising such a copolymer in its bulk and/or as a coating.

The invention also relates to particles obtained from such copolymers.

The present invention relates lastly to the resultant medical device, notably implantable.

Magnetic resonance imaging (MRI) is a medical imaging tool that makes it possible to obtain images of the human body owing to the presence of hydrogen atoms.

In order to increase the signal intensity and the quality of the images obtained, numerous contrast agents are used, for the most part soluble in biological fluids, which then allow better visualization in the body.

However, MRI is unable to visualize a large majority of the polymer-based prostheses or medical devices implanted in the body for the purpose of alleviating certain disorders, and consequently monitor their fate in the body.

Now, there is a need to be able to monitor the fate of these prostheses or implanted medical devices in order to evaluate the quality and durability of fixation, for example, cellular integration, as well as any degradation of the prosthesis.

Grafting of contrast agents on water-soluble polymers, which are not intended to remain in the body, has already been described. These water-soluble polymers substituted with complexing agents may in particular improve targeting and/or retention at the level of the organs to be investigated by MRI.

Thus, document US2007/0202047 describes a polyamine substituted with complexing agents, displaying an affinity for tumor cells.

Moreover, the document Irma Perez-Baena et al., "Single-chain polyacrylic nanoparticles with multiple Gd(III) centers as potential MRI contrast agents", Journal of Materials Chemistry, 2010, 20, 6916-6922, describes a contrast agent for MRI having improved relaxivity owing to its macromolecular structure in which Gd(III) ions are incorporated by complexation.

Amphiphilic copolymers optionally in the form of micelles, onto which complexes of paramagnetic ions are grafted, are also known from the documents Biomaterials 32 (2011) 6595-6605, Biomacromolecules 2007, 8, 3126-3134 and Journal of Applied Polymer Science, Vol. 120, 2596-2605.

So far this grafting technique has found little application for permanent visualization of implants that are intended to remain in the body.

However, a technique is known from document WO2011/004332 for a long-lasting application of visualization of solid objects implanted in the body, using chemical grafting of contrast agents on a polymer chain. Thus, this document relates to a hydrophobic polymer, characterized in that it comprises at least one monomer unit on which is grafted a paramagnetic-ion-chelating ligand complexed with said paramagnetic ion, said monomer unit possessing at least one carbonyl group, said monomer unit comprising, before grafting, at least one hydrogen atom in the α-position of said at least one carbonyl group and said grafting of the chelating ligand taking place at the level of said at least one hydrogen atom in the α-position of said at least one carbonyl group.

However, owing to the necessity of the presence of a hydrogen atom in the α-position of the carbonyl group, this technique is limited as to the choice of the nature of the polymer material used. Moreover, the copolymer is obtained by modification of the main chain and not by copolymerization of two different monomer units.

From documents US 2008/0073272 and WO 2008/034911, hydrophobic copolymers are also known that are visible by magnetic resonance imaging. However, these copolymers are crosslinked, and consequently are insoluble in all types of solvent. In other words, they belong to the class of thermosets or resins, not covered by the present application.

There is consequently a need to find hydrophobic thermoplastic polymers, in particular soluble in hydrophobic solvents, and visible by magnetic resonance imaging, that may be employed either in the bulk or on the surface of implantable medical devices, the associated technique for preparing said polymers being simple, and easy to carry out, in particular on a variety of polymers compatible with medical applications.

From document WO99/60920, coatings are known for medical devices for making them visible in MRI. The copolymers described in that document are obtained by surface functionalization of certain units of the polymer, and not by copolymerization of two different monomer units. This technique does not allow the amount of paramagnetic ions to be controlled.

There is thus a need to find hydrophobic thermoplastic polymers such as allow control of the amount of paramagnetic ions detectable on medical devices, in particular by controlling the degree of substitution of the contrast agent.

Thus, according to a first of its aspects, the present invention relates to a hydrophobic copolymer, notably useful for manufacturing and/or coating medical devices, notably implantable, characterized in that it comprises at least one first monomer unit and at least one second monomer unit, on which is grafted a paramagnetic-ion-chelating ligand that may complex with said paramagnetic ion or a paramagnetic-ion-chelating ligand complexed with said paramagnetic ion, the second monomer unit being grafted in sufficient amount for the copolymer to be visible in magnetic resonance imaging when it is complexed with said paramagnetic ion.

The present invention notably relates to a hydrophobic thermoplastic copolymer, notably useful for manufacturing and/or coating medical devices, notably implantable, characterized in that it is obtained by copolymerization, in that it comprises at least one first monomer unit and at least one second monomer unit on which is grafted a paramagnetic-ion-chelating ligand that may complex with said paramagnetic ion or a paramagnetic-ion-chelating ligand complexed with said paramagnetic ion, the second monomer unit being grafted in sufficient amount for the copolymer to be visible in magnetic resonance imaging when it is complexed with said paramagnetic ion.

"Sufficient amount" means the minimum amount allowing the required effect to be achieved, namely visibility in magnetic resonance imaging.

"Thermoplastic copolymer" means a linear or branched copolymer, forming a one- or two-dimensional network, which is characterized by a softening point. Resins, crosslinked or thermosetting copolymers are thus excluded from the definition of "thermoplastic copolymers".

In particular, the thermoplastic copolymers are soluble in hydrophobic solvents whereas the thermosetting copolymers are insoluble in all types of solvent.

"Copolymerization" means, in the sense of the invention, a polymerization reaction between at least two different monomers.

The invention also relates to a method of preparing said copolymer as defined above, comprising (i) at least one step of preparing, by copolymerization, a copolymer comprising at least one first monomer unit and at least one second monomer unit comprising a functional group capable of forming a bond, notably a stable bond, with a complex of a paramagnetic ion or with a paramagnetic-ion-chelating ligand that may complex with said paramagnetic ion, optionally by click chemistry and (ii) at least one step of grafting, on said second monomer unit, of a complex of a paramagnetic ion or of a paramagnetic-ion-chelating ligand that may complex with said paramagnetic ion.

When step (ii) consists of a step of grafting, on said second monomer unit, of a paramagnetic-ion-chelating ligand that may complex with said paramagnetic ion, said method comprises a step (iii) of complexation of said paramagnetic ion with said chelating ligand.

It also relates to a medical device, characterized in that it comprises at least one copolymer as defined above in its bulk and/or as a coating and/or as marking, notably for the purpose of traceability as explained below.

The invention also relates to a method of preparing a medical device, notably implantable, detectable in magnetic resonance imaging, characterized in that it comprises at least one step of coating with a copolymer as defined above, notably by dipping or by spraying, in a solution comprising said polymer according to the invention.

It further relates to a compound of the following formula (A) or of the following formula (B)

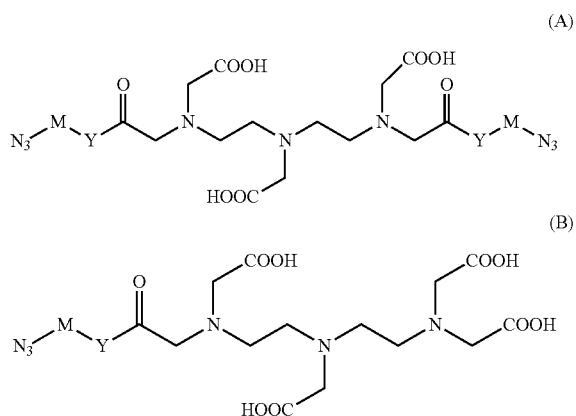

in which
M represents a group —(CHR)$_x$— or —(CH$_2$—CHR—O)$_y$, where x and y represent independently an integer between 1 and 18 for x and between 1 and 1000 for y, Y being a function among the functions capable of reacting with anhydride groups, for example the hydroxyl, amine or thiol groups, R being a (C$_1$-C$_{18}$)alkyl group or a hydrogen atom, notably useful as complexing agent of a paramagnetic ion.

The invention also relates to the corresponding complex of the following formula (A') formed from (A):

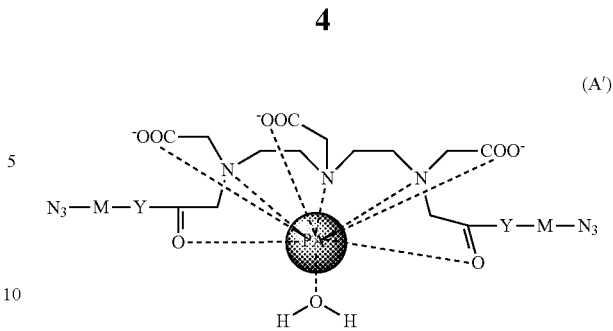

and, the corresponding complex of the following formula (B') formed from (B):

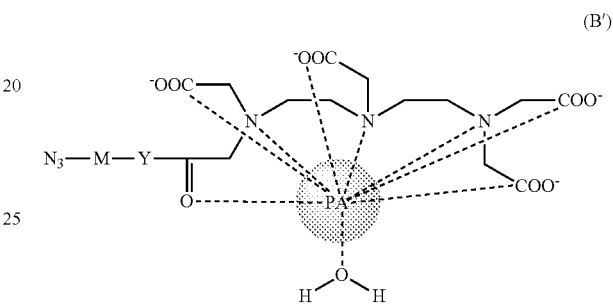

in which M and Y are as defined above, and
PA denotes a paramagnetic ion, notably gadolinium.

The copolymer according to the present invention, owing to the possibility of controlling the degree of functionalization provided by incorporating the second functionalized monomer unit, thus makes it possible to adapt the content of complex, and hence of contrast agent, to the nature both of the copolymer used and of the final implant, so as to obtain the required conditions of visualization, namely optimal contrast in the image.

The present invention also relates to particles comprising at least one copolymer according to the invention having an average size in the range from 1 nm to 1000 μm, preferably from 10 nm to 500 μm and in particular from 20 to 250 μm.

In the context of the present invention:
comprises the polymer "in its bulk", means that the object in question comprises within it a polymer of that kind, and for example consists essentially or partially of said polymer,
the term "polymer chain" denotes a macromolecule or a portion of a macromolecule comprising a linear or branched sequence of consecutive units located between two consecutive limiting units, each of which may be an end group, a branching point or a particular feature that is characteristic of the macromolecule,
the term "main polymer chain" denotes the portion of the polymer chain as defined above, before the grafting step,
the term "monomer" covers a molecule that may be converted to a polymer by combining with itself or with other molecules of the same type,
a "monomer unit" or "monomeric unit" denotes the smallest constituent unit, repetition of which leads to a regular macromolecule,
a "complexed monomer unit" denotes a monomer unit on which a complex is grafted, a "hydrolytically degradable" material denotes a material that degrades in the presence of water following breaking of the bond that joins the monomer units by hydrolysis and for which there is proof that the products of degradation of the material have number-average molecular weights lower than the number-average molecular weights of the polymer chains of the starting material, a "bio-absorbable" or "absorbable" material denotes a material that degrades enzymatically or hydrolytically and for which there is proof that the degradation products are integrated in biomass and/or eliminated from the body by metabolization or renal filtration, "block" denotes a portion of a macromolecule comprising several identical or different constituent units that possess at least one particular feature of constitution or of configuration allowing it to be distinguished from the portions adjacent to it, the terms "complexing agent of a paramagnetic ion", "chelating agent of a paramagnetic ion" or "paramagnetic-ion-chelating ligand" are equivalent, and denote molecules bearing one or more chemical functions allowing them to bind to one or more paramagnetic ions by a noncovalent interaction, for example of the Lewis acid/Lewis base type, electrostatic or other, the term "complex" denotes one or more cations surrounded by one or more ligands that delocalize a proportion of their electronic density on the cation or cations thus forming noncovalent chemical bonds, for example of the Lewis acid/Lewis base type, with the latter. In the context of the present invention, said cations are paramagnetic ions.

the terms "between . . . and . . . " and "vary from . . . to . . . " signify that the limits of the range are also described, "hydrophobic polymer" means a polymer for which a contact angle is measured between 40 and 180° and more preferably between 50 and 150°, for example according to the measurement protocol detailed below. Amphiphilic polymers or those forming micelles do not form part of the invention.

In other words, the copolymers according to the invention are insoluble in biological fluids.

Protocol for Measuring a Contact Angle

Figure 1:
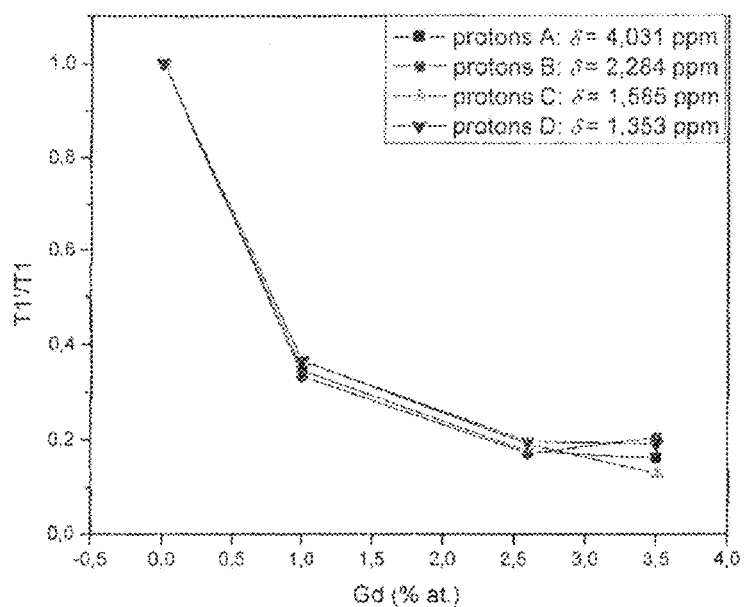
FIG. 1 shows the relative variation of the T1 values (T1'/T1) of PCL-[Gd(DTPA)] as a function of the gadolinium concentration.

The contact angle may be measured with a tensiometer, for example KRUSS K100 sold by the company KRUSS.

According to Wihelmy's method, a clean, dry glass microscope slide is immersed in a solution of copolymer according to the present invention, with a concentration of 5 g/L dissolved in tetrahydrofuran (THF), corresponding to an immersion of 1 cm in the water, this operation being carried out at 20° C.

The tensiometer measures the surface tension between the water and the slide covered with copolymer, and calculates the resultant contact angle with the water.

Novel Hydrophobic Copolymers

The hydrophobic thermoplastic copolymer according to the present invention is characterized in that it is a copolymer obtained by copolymerization of at least one first monomer and of at least one second functionalized monomer, on which a complex of a paramagnetic ion or a ligand that may complex a paramagnetic ion is grafted, optionally by click chemistry, after the copolymerization step.

In the context of the present invention, the copolymer thus comprises at least first units, called monomer units A, obtained from the first monomer, and at least second units, called monomer units B-F, obtained from the second monomer, in which B is a monomer unit and F is a functional group able to form a bond with a complex of a paramagnetic ion or a ligand that may complex a paramagnetic ion.

In the context of the present invention, the expression "functional group" denotes a group of atoms forming a reactive function.

"Degree of functionalization" means, in the context of the present invention, the content by number of monomer units B-F, relative to the total number of monomer units of the copolymer.

In the case when said grafting step has been carried out by click chemistry as explained below, "degree of functionalization" also denotes the content by number of monomer units grafted onto a paramagnetic-ion-chelating ligand that may complex with a paramagnetic ion or onto a paramagnetic-ion-chelating ligand complexed with a paramagnetic ion relative to the total number of monomer units of the copolymer.

In the examples given below, the influence of the degree of functionalization is illustrated by the percentage by weight of paramagnetic ion in the copolymer, i.e. the content by weight of paramagnetic ion relative to the total weight of the copolymer considered.

According to a particular embodiment, the degree of functionalization is between 0.01 and 50%, notably between 0.1 and 10%, or even between 0.1 and 5%.

Preferably, the hydrophobic thermoplastic copolymers according to the invention are soluble in at least one hydrophobic solvent. Example 14 below notably illustrates the solubility of a copolymer according to the invention in dichloromethane. The thermoplastic copolymers according to the invention may for example be soluble in chloroform, dimethylsulfoxide, N,N-dimethylformamide, acetone, tetrahydrofuran and/or ethyl acetate.

This solubility means that the copolymers according to the invention can easily be used as coating or in compositions for aerography.

The copolymers according to the invention may be linear, branched and/or star. According to a particular embodiment, the copolymers according to the invention are linear.

The invention relates to hydrophobic thermoplastic copolymers as defined above that may have various degradation profiles. In other words, depending on the nature of the copolymer envisaged, as is detailed below, it may be bioabsorbable or degradable hydrolytically or otherwise. This property may thus easily be modulated depending on the application envisaged, which constitutes one of the advantages of the present invention. Advantageously, this property may be evaluated using the following degradation test.

Degradation Test

This test makes it possible to determine whether a polymer is bioabsorbable or hydrolytically degradable according to the definition given above. This test consists of investigating the variation, for example by size exclusion chromatography, of the number-average molecular weights in conditions imitating a physiological situation (PBS buffer at pH 7.4, mechanical stirring at 37° C.).

The percentage decrease in the number-average molecular weight at different times is expressed by the following equation:

$$\% = \frac{\text{number-average molecular weight at } T_0 - \text{number-average molecular weight at } T}{\text{number-average molecular weight at } T_0}$$

As a guide, according to the present invention:
for a time T=2 months, the percentage decrease in the number-average molecular weight may be between 0 and 50%, preferably between 0 and 25%.
for a time T=6 months, the percentage decrease in the number-average molecular weight may be between 0 and 75%, preferably between 5 and 50%.
for a time T=1 year, the percentage decrease in the number-average molecular weight may be between 5 and 100%, preferably between 10 and 80%.
for a time T=2 years, the percentage decrease in the number-average molecular weight may be between 10 and 100%, preferably between 20 and 90%.

An illustration of application of the test is given in the following examples with respect to a copolymer according to the present invention.

First Monomer

In the case when the first monomer gives a degradable polymer, the first monomer must be biocompatible.

In the sense of the present invention, "biocompatibility" is the capacity of a material to induce an appropriate response from the host in a specific application. Moreover, in the context of the present invention, this relates to monomers conferring hydrophobic properties on the resultant copolymer.

Finally, since the intended implantation may be permanent or temporary, the copolymers employed in the context of the present invention may be biostable or bioabsorbable. Therefore the first monomer may be selected from monomers allowing biostable or bioabsorbable homopolymers to be obtained.

According to a particular embodiment, the first monomer is a monomer useful for preparing a polymer as defined below.

Monomers Useful for Preparing Biostable Homopolymers

Among the monomers useful for preparing biostable homopolymers, we may mention:

Monomers Useful for Preparing Polyolefins.

The polyolefins are hydrophobic linear aliphatic polymers represented by the following formula —($CH_2$—$C(RR')$)— in which R and R' may be hydrogen atoms or alkyl groups, more particularly ($C_1$-$C_{18}$)alkyl groups. The semicrystalline thermoplastics such as poly(ethylene) (PE) and poly(propylene) (PP) are the most used in the biomedical field. PE is chemically inert, resistant to oxidation and its density may vary depending on the manner of manufacture.

Monomers Useful for Preparing Fluoro Polymers.

The fluoro polymers are characterized by their chemical inertness and very weak intermolecular interactions. The perfluorinated chains are more hydrophobic and more stable than their hydrogenated homologs. Poly(tetrafluoroethylene) (PTFE) is the fluoro polymer most used in medicine. The anti-adhesion properties of PTFE prostheses are made use of for specific applications.

Monomers Useful for Preparing Acrylic and Methacrylic Polymers.

In the biomedical field, poly(methyl methacrylate) (PMMA) and poly(methyl acrylate) are the most representative of the methacrylic and acrylic derivatives. PMMA is a thermoplastic notably used in orthopedic surgery for its mechanical properties similar to bone. Its optical properties are moreover utilized for making intraocular implants.

Monomers Useful for Preparing Vinyl Polymers.

Monomers Useful for Preparing Semi-Aromatic Polyesters.

The semi-aromatic polyesters are nondegradable polyesters. In this category, poly(ethylene terephthalate) (PET) and poly(butylene terephthalate) (PBT) are predominantly used in the biomedical field. PET in the amorphous (transparent) or semicrystalline (x=30%) state displays a low degree of water absorption, chemical inertness and good properties of mechanical strength.

Monomers Useful for Preparing Polyurethanes (PUR).

The polyurethanes are block copolymers, made up of flexible units and of rigid units. They are light, flexible at low temperature and resistant to hydrolysis. Since the 1970s, the PURs have found numerous applications in surgery, owing to their properties of stability and biocompatibility.

Monomers Useful for Preparing Silicones.

The silicones or polysiloxanes are a group of polymers with very varied properties, having in common the siloxane unit —($Si(R_2)$—O)—,
with R representing independently a ($C_1$-$C_{18}$)alkyl group.

The strong silicon/oxygen bond of the unit endows the silicones with good chemical stability and resistance to aging. The properties of adherence of the silicones may be modulated depending on the nature of the substituents R. Thus, liquid compounds or gels, in the form of rubber (bandages) or in hard form may be obtained.

Monomers Useful for Preparing Bioabsorbable Homopolymers

The aliphatic polyesters are the absorbable materials most used in the biomedical field. They belong to a family of polymers that comprises both compounds produced by a bacterial route, the poly($\beta$-hydroxy acids), and synthetic compounds obtained either by polycondensation of hydroxy acids or of diacids and diols, or by opening of heterocycles of the lactone type.

In fact, depending on the nature of the polyester, absorption may take from 1 month to 10 years. The polyesters having an absorption time measured according to the protocol presented above greater than 1 month, or even 6 months, are more particularly intended in the context of the present invention.

We may mention in particular the polyester polymers consisting wholly or partly of identical or different monomer units, each of these units having the following formula (II):

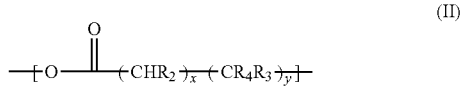

(II)

in which:

$R_2$, $R_3$ and $R_4$ represent independently a hydrogen atom, a ($C_1$-$C_{12}$)alkyl group or a ($C_1$-$C_8$)cycloalkyl group optionally substituted with a ($C_1$-$C_{12}$)alkyl group, x represents an integer between 0 and 12, for example between 0 and 6, and y represents an integer between 0 and 8, for example between 0 and 6, it being understood that x and y are not zero simultaneously.

In general, the polyesters of formula (II) may be obtained:

a) by polycondensation of a hydroxy acid on itself, or b) by polymerization by opening the lactone ring.

Among these polymers comprising monomer units of formula (II), we may notably mention the polyesters consisting wholly or partly of identical or different monomer units, each of the units having the following formula (III)

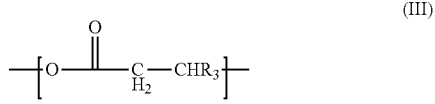

(III)

in which $R_3$ represents a ($C_1$-$C_{12}$)alkyl group.

Among the monomers useful for preparing polyesters, we may notably mention hydroxybutyric acid, hydroxyvaleric acid, hydroxyhexanoic acid and hydroxyoctanoic acid.

The following table shows the correspondence between the meaning of group $R_3$ and the full name of the polymer of formula (III).

| $R_3$ | Name of the polymer |
|---|---|
| $CH_3$ | Polyhydroxybutyrate (PHB) |
| $C_2H_5$ | Polyhydroxyvalerate (PHV) |
| $C_3H_6$ | Polyhydroxyhexanoate (PHHx) |
| $C_5H_8$ | Polyhydroxyoctanoate (PHO) |

As an illustration of other polyesters comprising monomer units of formula (II), we may mention the polyesters obtained by opening lactone rings of formula (IV)

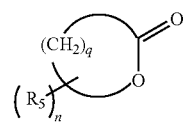

(IV)

in which:

q represents an integer that may vary between 2 and 9, $R_5$ represents a ($C_1$-$C_{12}$)alkyl group, and n is an integer between 0 and 2, it being understood that when n is equal to 2, the two groups $R_5$ not only may be different but also may be located on the same or on two different carbon atoms.

When q is equal to 5 and n is equal to 0, it is the caprolactone or ϵ-caprolactone.

The polyesters thus obtained are polycaprolactone or poly(ϵ-caprolactone). Among the lactones of formula (IV) that may be suitable for the present invention, we may moreover mention δ-valerolactone, γ-butyrolactone, ϵ-decalactone, pivalolactone and diethylpropriolactone.

As an illustration of other polyesters comprising monomer units of formula (II), we may mention the polymers of lactic acid (PLA) consisting wholly or partly of identical or different monomer units, each of these units having the following formula:

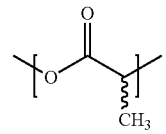

Generally the polymers of lactic acid are obtained from the lactide monomer, for example by ring-opening polymerization or from lactic acid or from derivatives of lactic acid by polycondensation. Owing to the chiral nature of lactic acid, there are poly-L-lactide (PLLA) and poly-D-lactide (PDLA), poly(D,L lactide), poly-meso-lactide and all the stereoisomers that form part of the polymers suitable for the present invention.

As a further illustration of other polyesters of formula (II), we may mention the polymers of glycolic acid or poly (glycolide) consisting wholly or partly of identical or different monomer units, each of these units having the following formula

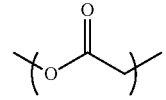

Among the polyesters comprising monomer units of formula (II) usable in the context of the invention, we may also mention the homopolymers and copolymers of p-dioxanone (1,4-dioxan-2-one); 1,4-dioxepan-2-one (including its 1,5,8, 1,2-tetraoxacyclotetradecane-7,1,4-dione dimers); 1,4-dioxepan-5-one; 1,5-dioxepan-2-one; 6,6-dimethyl-1-4-dioxan-2-one; 2,5-diketomorpholine; 3-methyl-1,4-dioxane-2,5-dione; 3,3-diethyl-1,4-dioxane-2,5-dione; 6,6-dimethyl-dioxepan-2-one and polymer blends thereof.

The following table lists the main types of aliphatic polyesters:

| Type of aliphatic polyesters | Polymers and acronyms | Structures |
|---|---|---|
| Poly(α-hydroxy acids) | Poly(glycolide) PGA | 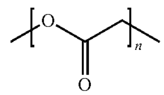 |
| | Poly(lactide) PLA | |
| Poly(β-hydroxy acids) | Poly(hydroxybutyrate) PHB | 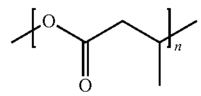 |
| | Poly(hydroxyvalerate) PHV | |
| | Poly(β-malic acid) | |
| Poly(γ-hydroxy acids) | Poly(valerolactone) PVL | 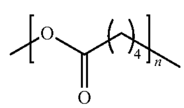 |
| Poly(ε-hydroxy acids) | Poly(ε-caprolactone) PCL | |
| | Poly(ε-decalactone) PDL | |
| Others | Poly(1,4-dioxane-2,3-dione) | 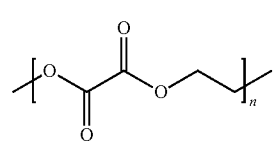 |
| | Poly(para-dioxanone) PDS | |

The poly(lactide) (PLA), poly(glycolide) (PGA), poly(ε-caprolactone) (PCL) and their copolymers are the most used poly(hydroxy acid)s on account of their biocompatibility and their wide range of properties.

According to a particular embodiment of the invention, ε-caprolactone is used as first monomer.

Certain aliphatic polyamides, in particular the polypeptides, are also a class of potentially hydrophobic degradable polymers coming within the scope of the present invention.

Functionalized Monomer

The functionalized monomer selected is a monomer that can comprise a functional group allowing grafting of a complex of a paramagnetic ion or of a ligand that may complex said paramagnetic ion, via said functional group, optionally by click chemistry.

Said functionalized monomer may or may not be hydrophobic.

The monomer used without the functional group may be selected from any one of the monomers mentioned as first monomer.

According to a particular embodiment, the functionalized monomer used without the functional group is selected from a monomer useful for preparing a polyester, according to the above description for the first monomer.

In the context of the present invention, the functional group may be any reactive function known by a person skilled in the art, and notably a nitride, alkyne, nitrile, carboxylic acid, ester, anhydride, acid halide, amide, iso(thio)cyanate, epoxide, thiol, amine, aziridine, ketone, aldehyde, diene, alkene function or else hydroxyl function, which may or may not be protected.

The grafting step is described below.

As functionalized monomer, it is possible to use a propargyl ε-caprolactone (αPr εCL) or 5-NHZ-δ-valerolactone (5-NHZ-δ-VL).

Complexing Agent/Functionalized Complex

The complexing agent is selected in relation to the type of grafting envisaged.

Thus, according to a particular embodiment, when grafting of the click chemistry type according to the Huisgen reaction is envisaged, the complex of a paramagnetic ion must comprise at least one nitride function if the functionalized monomer contains an alkyne function.

The complexing agent before complexation that may be used in the context of the present invention may possess at least one carboxylic acid function. For this, we may notably mention diethylenetriaminepentaacetic acid (DTPA), tetraazacyclododecanetetraacetic acid (DOTA) and tetraazacyclotetradecanctetraacetic acid (TETA).

The paramagnetic ion suitable for the present invention is a polyvalent paramagnetic metal including, but not limited to the lanthanides and the transition metals such as iron, manganese, chromium, cobalt and nickel.

Preferably, this paramagnetic ion is a lanthanide that is highly paramagnetic and, even more preferably, it is a gadolinium(III) ion.

As examples of complexing agent, we may mention the novel compounds DTPA-monoN$_3$ and DTPA-diN$_3$, which form part of the invention. The corresponding complexes [Gd(DTPA-monoN$_3$)] and [Gd(DTPA-diN$_3$)], are also novel, and form part of the invention. DTPA-diN$_3$ and [Gd(DTPA-diN$_3$)] are as shown below:

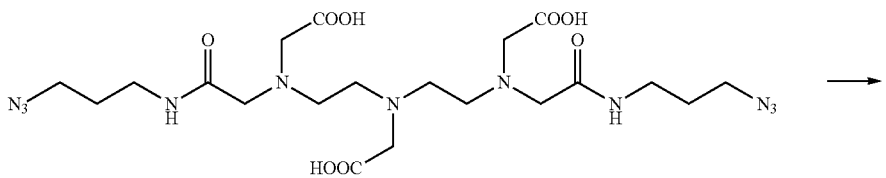

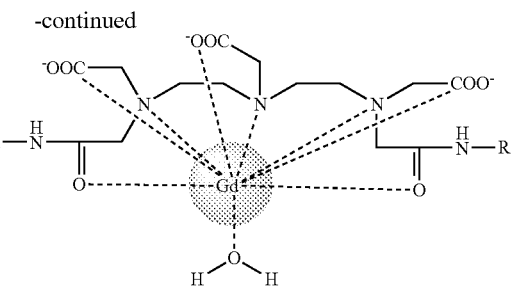

with R=—(CH$_2$)$_3$N$_3$
and DTPA-monoN$_3$ and [Gd(DTPA-monoN$_3$)] are as shown below:

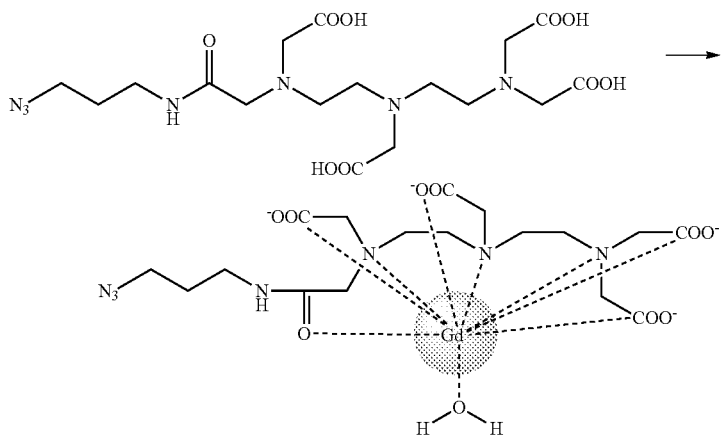

The gadolinium complex [Gd(DTPA-diN$_3$)] may be obtained by bringing the chelating ligand DTPA-diN$_3$ into contact with GdCl$_3$ in water containing pyridine, in the presence or absence of a solvent such as DMF, DMSO, for example at a temperature between 20 and 60° C., for example at 40° C., for a time that may be between 30 min and 1 week, for example for a time of 24 hours.

As other examples of complexes of a paramagnetic ion, we may mention the complexes of europium salts (Eu$^{3+}$).

Copolymer According to the Invention

In the context of the present invention, the copolymers according to the invention may have a number-average molecular weight between 1000 and 500 000, notably between 2000 and 100 000 and for example between 3000 and 50 000 g/mol.

The nature of the first and of the second monomer is advantageously selected so that the latter can give rise to a reaction of copolymerization, which follows from the general knowledge of a person skilled in the art.

According to a particular embodiment of the invention, the copolymer is a bioabsorbable copolymer.

The copolymer may be a random copolymer or a block copolymer or a graft copolymer.

All of these copolymers can be produced according to protocols and conditions known by a person skilled in the art.

As examples of copolymer according to the present invention we may mention in particular the following copolymers:

random copolymer of caprolactone (CL) and propargyl caprolactone (CL-propargyl or Pr-CL), block copolymer of caprolactone (CL) and propargyl caprolactone (CL-propargyl or Pr-CL), random copolymer of caprolactone (CL) and 5-NH$_3$$^+$-δ-valerolactone (5-NH$_3$$^+$-δ-VL), or else block copolymer of caprolactone (CL) and 5-NH$_3$$^+$-δ-valerolactone (5-NH$_3$$^+$-δ-VL).

According to a particular embodiment of the invention, the copolymer is a random copolymer.

According to a first particular embodiment of the invention, A and B are identical.

According to a sub-embodiment of this first embodiment of the invention, A and B are both obtained from cyclic esters as defined above.

As copolymer, we may notably mention the copolymer obtained by copolymerization of an ε-caprolactone and an α-propargyl ε-caprolactone according to the following scheme:

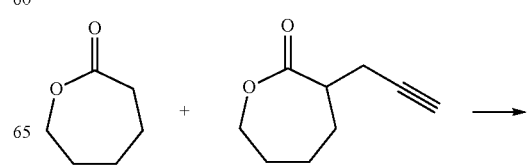

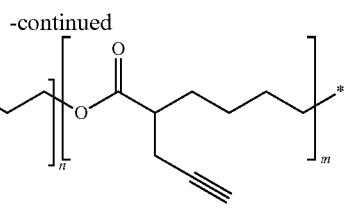

The copolymer may be obtained by bringing the two monomers into contact, in the presence of a catalyst such as Sn(Oct)₂ (where "Oct" is octanoate) and in the presence or absence of an initiator such as isopropanol and of a solvent such as toluene, at a temperature that may be between 0 and 200° C., for example at 140° C. for a period between 1 min and 1 week, for example for 3.5 hours.

According to an even more particular embodiment of the invention, the polymer according to the invention is a copolymer of ε-caprolactone and of α-propargyl ε-caprolactone with a number-average molecular weight between 1000 and 500 000, in particular between 3000 and 50 000 g/mol.

According to another sub-embodiment of this first particular embodiment of the invention, A and B are both obtained from methyl acrylate.

We may notably mention, as copolymer, the copolymer obtained by copolymerization of methyl acrylate and propargyl acrylate according to the following scheme:

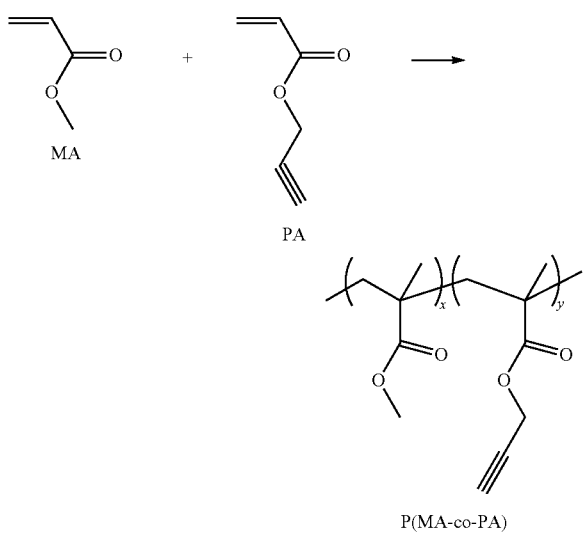

The copolymer may be obtained by bringing the two monomers into contact, for example by a conventional radical polymerization or a controlled radical polymerization (RAFT or ATRP).

In the case of a conventional polymerization, the latter may be carried out in the presence of a radical generator, for example AIBN or benzoyl peroxide, in a solvent notably of the toluene or dioxane type at temperatures that may be between 60 and 110° C. The reaction time may be between 5 minutes and 15 hours.

In the case of a so-called controlled radical polymerization, for example ATRP, polymerization may be carried out in the presence of a halogenated initiator, for example alpha-isobutyryl bromide, of a catalytic system based on copper such as the CuBr/PMDETA complex in a solvent, for example toluene, at temperatures between 60 and 90° C. The reaction time may be between 1 and 5 hours.

According to an even more particular embodiment of the invention, the polymer according to the invention is a copolymer of methyl acrylate and propargyl acrylate with a number-average molecular weight between 5000 and 100 000 g/mol.

When said copolymer has been obtained by a conventional radical polymerization, the number-average molecular weight may be between 60 000 and 100 000 g/mol, in particular between 70 000 and 90 000 g/mol.

When said copolymer has been obtained by a controlled radical polymerization, the number-average molecular weight may be between 5000 and 20 000 g/mol.

According to a second particular embodiment of the invention, A and B are different.

According to a sub-embodiment of this second embodiment of the invention, A and B are both obtained from cyclic esters as defined above.

We may notably mention, as copolymer, the copolymer poly(5-NH₃⁺-δ-valerolactone-co-ε-caprolactone) obtained by copolymerization of an ε-caprolactone and an amino δ-valerolactone according to the following scheme:

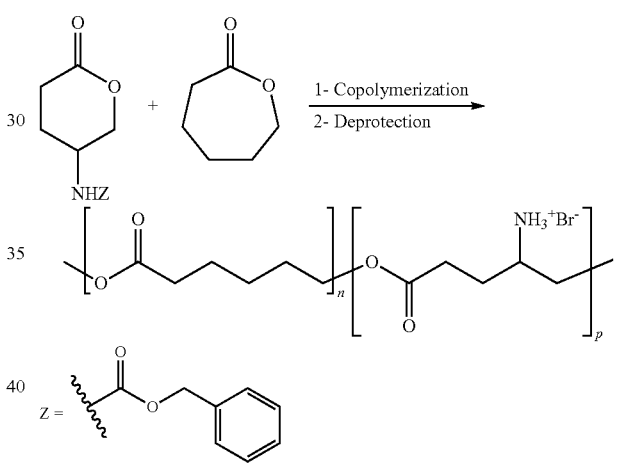

The copolymer may be obtained by bringing the two monomers into contact in the presence of a catalyst such as Sn(Oct)₂ and in the presence or absence of an initiator such as benzyl alcohol and of a solvent such as tetrahydrofuran at a temperature that may be between 0 and 200° C., for example at 110° C. for a period between 1 min and 1 week, for example for 24 hours.

The deprotection of the amine functions to ammonium functions may be carried out according to protocols and conditions known by a person skilled in the art, for example by reaction of the protected copolymer with hydrobromic acid in a solvent such as dichloromethane at room temperature for 20 minutes.

According to an even more particular embodiment of the invention, the polymer according to the invention is a copolymer of ε-caprolactone and amino δ-valerolactone with a number-average molecular weight between 1000 and 500 000, in particular between 3000 and 50 000 g/mol.

The degree of functionalization, regardless of the embodiment, may be modulated.

In particular, in the case of a copolymer of ε-caprolactone and α-propargyl ε-caprolactone or of a copolymer of ε-caprolactone and amino δ-valerolactone, the degree of functionalization may vary between 0.01 and 50%, notably between 0.1 and 10%, or even between 0.1 and 5%.

As will become clear on reading the examples, it was found that, in comparable conditions of synthesis of the copolymer and of environment, the degree of functionalization has an influence on the proton relaxation time in NMR. Moreover, at the stage of MRI visualization, the degree of functionalization has an influence on the contrast of the image obtained. Thus, it was observed that beyond a certain value of the degree of functionalization, image contrast is not improved.

According to a particular embodiment, the copolymer according to the present invention may also comprise additional monomer units, also biocompatible. These additional monomer units may take the form of additional blocks. Among the latter, we may notably mention the following polymer blocks: poly(ethylene glycol), poly(propylene glycol) or poloxamer.

According to a variant of the invention, the additional block is a poly(ethylene glycol) or PEG block of formula $H(OCH_2CH_2)_pOH$, where p varies from 5 to 600.

Method of Grafting of the Chelating Ligand or of the Agent Complexed with a Paramagnetic Ion The method of grafting generally consists of coupling a ligand, complexed or not with a paramagnetic ion, with the functionalized monomer units of the copolymer obtained by copolymerization of at least one first monomer and at least one functionalized monomer.

During said grafting, there may for example be formation of a linkage function or of a covalent bond.

"Linkage function" denotes a chemical function whose formation makes it possible to attach, by covalent bonding, two chemical entities that are originally separate.

According to a particular embodiment, grafting is provided by means of one or more bonds that are not hydrolyzable in the physiological environment. In other words, stable bonds are preferred for carrying out the present invention.

According to a particular embodiment, the linkage function or the bond between the complexing agent and the monomer to which it is attached is at least as stable as the bonds of the main chain, i.e. at least one functionalized complex is not eliminated from the body before the polymer itself degrades.

In the context of the present invention, "stable bond" means a bond that is not destroyed after undergoing the stability test as described below:

Stability Test

Thirty (30) tubes are charged with a defined amount of copolymer complexed with the paramagnetic ion (for example $Gd^{3+}$), for example 50 mg for each tube, to which 5 ml of phosphate-buffered saline or PBS is added. These tubes are then put in a stove at 37° C. with stirring to simulate physiological conditions.

3 tubes correspond to a degradation time:

| |
|---|
| 7 days |
| 15 days |
| 30 days |
| 60 days |
| 90 days |
| 150 days |
| 210 days |
| 270 days |
| 330 days |
| 400 days |

Inductively-coupled plasma-mass spectrometry or ICP-MS of the aqueous phase is carried out for each sample; this measures the amount of paramagnetic ion released in the aqueous phase in complexed or free form. In the absence of paramagnetic ion determined in the release medium, this is proof that the polymer-complex bond is stable, in particular at least as stable as the intra-copolymer bond, and that the complex is not decomplexed.

According to a particular embodiment of the invention, grafting is carried out by simple coupling, for example by click chemistry.

Grafting may moreover be carried out by any simple method that is an alternative to click chemistry, notably by amidations or esterifications.

Moreover, according to a particular embodiment, the present invention also comprises the copolymers comprising a linker between the ligand and the functionalized monomer unit. It may be included in the structure of the copolymer with a view to removing the ligand from the main chain. The following groups may notably be mentioned as linkers: alkyl chains, polymer chains, in particular polyether chains, in particular PEG or pluronic.

As linkage function resulting from a reaction of click chemistry (Lclick), we may notably mention triazole, tetrazole, thioether, carbamate or urea.

For example, a linkage function Lclick may be obtained, according to the invention, from the reaction of click chemistry between a functional group Y and a complementary functional group F, and allow joining a complex of a paramagnetic ion or a paramagnetic-ion-chelating ligand that may complex with said paramagnetic ion according to the invention and a copolymer according to the invention.

For example, the reaction of click chemistry may be represented by the following scheme, in the case when the complexing agent is of the monodentate type.

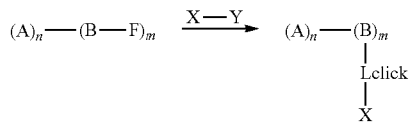

in which n and m represent the number of monomer units A and B-F respectively, where n may vary from 5 to 4500, for example from 10 to 1000 and m may vary from 1 to 500, for example from 1 to 10, A represents a first monomer unit, B-F represents a second monomer unit, in which the functional group F is the functional group that reacts with the functional group Y by click chemistry to form the linkage function Lclick.

Lclick represents the linkage function obtained by click chemistry between the functional groups F and Y, and X-Y represents a complex of a paramagnetic ion or a paramagnetic-ion-chelating ligand that may complex with said paramagnetic ion in which the functional group Y is the functional group that reacts with the functional group F by click chemistry to form the linkage function Lclick.

According to one embodiment, the reaction of click chemistry employed according to the invention may be:
- a reaction of cycloaddition of unsaturated species, in particular a reaction of 1,3-dipolar cycloaddition or a reaction of the Diels-Alder type;
- a reaction of nucleophilic substitution, in particular a reaction of opening of constrained electrophilic heterocycles such as epoxides, aziridines, aziridinium ions and episulfonium ions;

a reaction on the carbonyls with the exception of aldol chemistry, in particular a reaction of formation of ureas, thioureas, aromatic heterocycles, oxime ethers, hydrazones or amides; or a reaction of addition on multiple carbon-carbon bonds, in particular a reaction of epoxidation, dihydroxylation, aziridination, addition of sulfenyl halide, addition of thiol or else addition of the Michael type.

In the case of a reaction of cycloaddition, a nitride group may be reacted either with an alkyne group leading to formation of a triazole linkage function, or with a nitrile group, leading to formation of a tetrazole.

The reaction most widely used in click chemistry, which may be employed in the context of the present invention, is the Huisgen reaction "cycloaddition of alkynes on nitrides", described in R. Huisgen Angew. Chem. 1963, 75, 604 according to the following scheme:

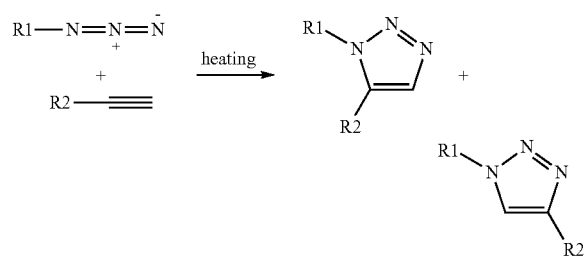

and according to another catalyzed version described in V. V. Rostovtsev, L. G. Green, V. V. Fokin, K. B. Sharpless, Angew. Chem. Int. Ed. 2002, 41, 2596 and C. W. Tornøe, C. Christensen, M. Meldal, J. Org. Chem. 2002, 67, 3057 according to the following scheme:

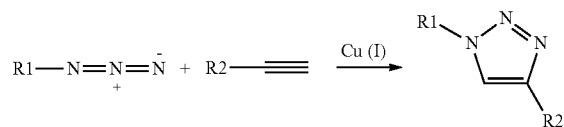

Thus, according to a particular embodiment of the invention, the aim is to form a copolymer comprising a monomer unit functionalized with a propargyl functional group.

Accordingly, by reacting a complex of a nitride-functionalized paramagnetic ion, or of a nitride-functionalized ligand that may complex said paramagnetic ion with the monomer units functionalized with a propargyl functional group, a copolymer is obtained that is a complex of a paramagnetic ion or that may complex a paramagnetic ion.

Medical Device

The present invention extends to a medical device comprising at least one polymer according to the present invention.

The polymer according to the present invention may form an integral part of the medical device in itself; in other words it is comprised in its bulk or else is on the surface of said device in the form of a coating with a thickness such that it enables the medical device to be made visible in magnetic resonance imaging.

Typically, the coating may form a thickness between 1 and 1000 µm, for example between 10 and 100 µm.

In the variant consisting of coating the medical device, various methods may be employed that are known per se by a person skilled in the art. In this connection, we may mention electrospinning, dipping, the application of spray drying or aerography or spraying.

Of course, the present application extends to medical devices that have undergone another type of treatment in the bulk and/or on the surface of a different nature to that considered in the present invention. As an example, we may mention treatments against bacterial and fungal adhesion, treatments allowing release of active principles such as antibiotics, antibacterials, antifungals, anti-inflammatories, and any kind of active principles that may be released in situ.

As medical devices particularly suitable for the present invention, we may mention the medical devices that more particularly find application in the field of gynecology, for example for mesh or prostheses for genital prolapse.

According to another aspect, the present invention extends to a method of marking a medical device, characterized in that it comprises at least one step of depositing a polymer according to the invention, notably on a targeted zone of the medical device, on the surface of the material.

According to this aspect, the polymer according to the invention is thus deposited on the prostheses, notably in the form of an inscription in order to effect post-operative monitoring owing to the direct marking on the material.

More particularly, the marking may be intended for traceability of the medical device. The medical device may thus be identified throughout its life, whether during manufacture, distribution or else following placement. Thus, the marking may take any form or surface on the medical device.

Even more particularly, the inscriptions may take the form of numerals, of letters or of any other type of characters useful for traceability.

Figure 9A:
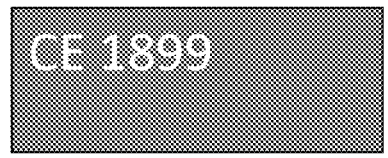
FIGS. 9A and 9B show examples of the marking according to one of the invention.
Figure 9B:
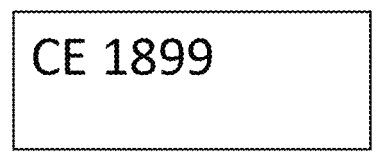

As examples, marking may be carried out according to the one of the following methods:

deposition of a homogeneous surface of polymer according to the invention on the surface of the material, in which the characters are inscribed (see FIG. 9A).

deposition of the characters on the surface of the material by techniques of micro-printing, in which the polymer according to the invention represents the ink (see FIG. 9B).

This aspect of the invention is particularly advantageous, in that the marking is thus integral with the medical device and not with the packaging of the latter as is usually the case.

The invention also extends to a medical device provided with marking carried out using a polymer according to the present invention.

The copolymer according to the present invention may also find application in any field of medicine where MRI is used.

These various fields may be classified by surgical specialties or by type of materials, notably implantable, that are used in several areas of medicine.

Classification by Medico-Surgical Specialties:
Gynecology:
 supporting mesh in the treatment of genito-urinary and rectal prolapse (vaginal and abdominal surgery)
 clips for tubal sterilization
 devices for tubal obstruction by the endo-luminal route
 strip for cervical cerclage
 intraperitoneal and intrauterine anti-adhesion devices
Urology:
 artificial urinary sphincter
 penile prosthesis
 patch for reinforcement of the corpora cavernosa (treatment of curvature of the penis, Peyronie's disease)

peri-urethral balloons
peri-urethral injectable devices
sub-urethral strips
stents, endo-urethral prostheses
tubes for urinary bypass (transcutaneous and natural ducts).
Orthopedics:
synthetic ligaments
new cartilage or joint
synthetic intervertebral disks
femoral head
acetabulum (femur and humerus)
tibial plateau
humeral head.
ENT:
cochlear implants
inner ear prostheses, bone substitutes.
Endocrinology:
implantable pumps.
Vascular:
endovascular prostheses
arterial and venous prostheses
devices for closure and hemostasis of transarterial vascular access
casings and catheters of chambers of implantable vascular access.
Neurology:
vascular stents
devices for occlusion of aneurysm and arterial vascular dissection
probes for electrostimulation
patches and reinforcements of dura mater and meninges.
Ophthalmology:
synthetic corneas.
Digestive Tract Surgery:
reinforcing plates (mesh) for hernia (diaphragm, parietal, inguinal, crural)
gastric rings
splenic threads
esophageal prostheses
stents for biliary tract and GIT (small intestine, colon, rectum) endoprosthesis
tubes for parenteral nutrition
artificial anal sphincter.
Cardiology:
coronary stents
pacemaker cases and probes
systolic pacing probes
Radiology:
agents for vascular embolization, for vascular occlusions (arterial or venous) (temporary or permanent).
Implantable Materials Used in Several Areas of Medicine:
wires for surgical sutures.
venous and arterial catheters (central and peripheral).
intracorporeal thermal probes.
surgical drains, tubular and plates, drainage channels.
synthetic clamps for approximation, for positioning, for digestive anastomosis and for prosthetic fixation.
tissue engineering: matrix for supporting stem cells in reconstructive surgery.

The copolymer according to the invention may finally find application in the actual enclosure of the MRI equipment.

The working environment in the MRI room necessitates absence of metals capable of disturbing the magnetic field of the MRI. This environment notably requires the development of metal-free, MRI-compatible equipment for ventilation and resuscitation. We may mention in this connection the following equipment: table, headrest, collar, splint, staples, supports and blocks for positioning and locating in MRI.

As stated above, the present invention also relates to particles comprising at least one copolymer according to the invention having an average size in the range from 1 nm to 1000 µm, preferably from 10 nm to 500 µm and in particular from 20 nm to 250 µm.

Any method of obtaining nanoparticles and/or microparticles known by a person skilled in the art is conceivable for obtaining the particles according to the invention. As an example, we may notably mention the spray-drying method or the nanoprecipitation method.

Production of the particles according to the invention by the nanoprecipitation method may take place as follows:

Said particles may be obtained by preparing two solutions, followed by mixing of them with stirring.

The first solution may contain a copolymer according to the invention, and optionally the same copolymer before grafting the ligand if we wish to obtain particles with a reduced proportion of gadolinium. This solution may also contain a surfactant such as sorbitan mono-(9Z)-9-octadecenoate for example and a solvent. Any solvent that dissolves the copolymer is suitable, such as acetone for example.

The second solution may contain a surfactant such as sorbitan polyoxyethylene monooleate (20) for example and a solvent. Any solvent in which the copolymer is not soluble is suitable, such as distilled water for example.

The two solutions may then be homogenized with magnetic stirring for a time for example from 1 hour to 10 hours. The first solution may then be poured dropwise into the second with magnetic stirring. The mixture is stirred for a time that may range from 1 to 10 hours and then the volatile solvent or solvents such as acetone for example may be evaporated under vacuum at room temperature. The solution may then be dialyzed for a time that may range from 6 hours to 1 week for example against distilled water prior to lyophilization.

The following examples illustrate the invention without limiting its scope.

EXAMPLES

In the examples given below, as well as throughout the present application:
"Pr" denotes propargyl,
"CL" denotes caprolactone,
"εCL" denotes ε-caprolactone
"PCL" signifies poly(ε-caprolactone)

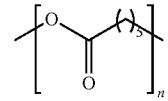

"P" signifies poly
"co" signifies copolymer
"VL" denotes valerolactone

Example 1

Preparation of a Ligand of Nitride-Functionalized Diethylenetriaminepentaacetic Acid (DTPA) (or DTPA-diN$_3$) 2

Step 1: Synthesis of 1-azido-3-aminopropane 1

Synthesis is carried out according to the following reaction scheme:

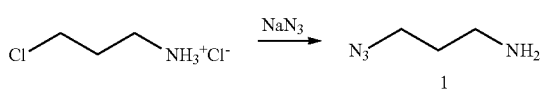

This compound was obtained according to a synthesis previously described by Carboni, B. et al. (*Macromolecules, Vol.* 40, No. 16, 2007/Carboni, B.; Benanlil, A.: Vaultier, M. *J. Org. Chem.* 1993, 58, 3736). An aqueous solution (30 mL) of 3-chloropropylamine hydrochloride (4 g; 30.8 mmol) and of sodium nitride (6 g; 92.3 mmol, 3 equiv) is heated at 80° C. for 17 h. After evaporation of the water, the reaction mixture is put in an ice bath. 50 mL of diethyl ether and 4 g of potassium hydroxide are added. The phases are separated. The product is extracted from the aqueous phase with 2*20 ml, of diethyl ether. The organic phase is then dried over magnesium sulfate and filtered. After evaporation, the oil obtained is purified by distillation at reduced pressure. (2.46 g; yield: 80%; colorless oil)

$^1$H NMR (300 MHz, CDCl$_3$), δ (ppm): 3.33 (t, 2H, CH$_2$N$_3$); 2.55 (t, 2H, CH$_2$NH$_2$); 2.34 (s, 2H, NH$_2$); 1.55 (q, 2H, CH$_2$CH$_2$CH$_2$).

FT-IR (ATR, cm$^{-1}$): 2100 (N$_3$)

Step 2: Synthesis of DTPA-diN$_3$ 2

Synthesis is carried out according to the following reaction scheme:

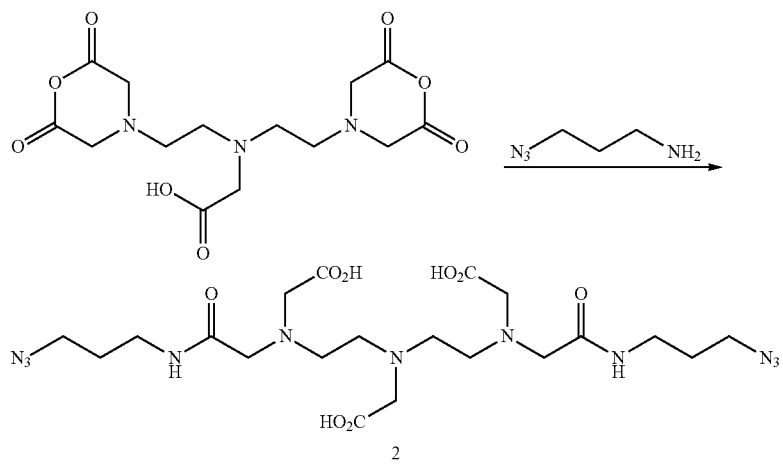

This compound was obtained according to a procedure described by I. Perez-Baena et al. (*J. Mater. Chem.*, 2010, 20, 6916-6922).

DTPA dianhydride (1 g; 2.8 mmol) and 1-azido-3-aminopropane (0.616 g; 6.2 mmol; 2.2 equiv.) are dissolved in anhydrous dimethylformamide (DMF) (20 mL) and stirred for 24 h at room temperature under argon. Then the DMF is evaporated, the crude reaction product is taken up in water and lyophilized. A white solid is then obtained (1.48 g; yield: 95%). $^1$H NMR (300 MHz, DMSO), δ (ppm): 3.4 (6H, CH$_2$CO$_2$H); 3.1 (12H, N(CH$_2$)$_2$N and NCH$_2$C(O)); 2.8 (8H, CH$_2$NHC(O) and CH$_2$N$_3$); 1.7 (4H, CH$_2$CH$_2$N$_3$).

FT-IR (ATR, cm$^{-1}$): 2100 (N$_3$)

LC-MS (ES+, m/z): 558.4 [M+H$^+$](calculated 558.27)

Example 2

Preparation of a [Gd(DTPA-diN$_3$)H$_2$O] Complex 3

Synthesis is carried out according to the following reaction scheme:

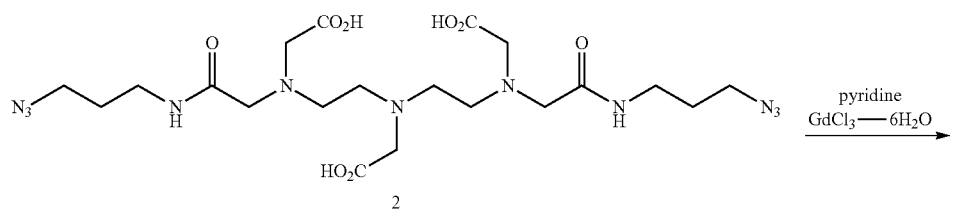

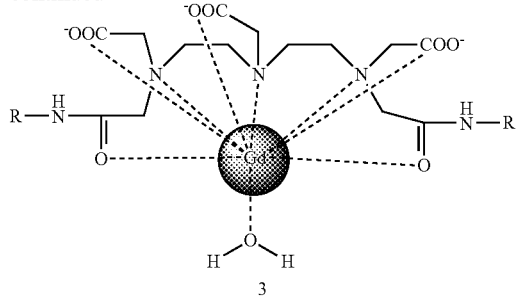

with R+(CH$_2$)$_3$N$_3$

Pyridine (1.44 mL; 17.9 mmol) is added to an aqueous solution of ligand (2; 1 g; 1.79 mmol). After stirring for 10 minutes at room temperature, GdCl$_3$·6H$_2$O (1.33 g, 3.58 mmol; 2 equiv) is added to the reaction mixture, which is then stirred for 24 h at 40° C. The water and pyridine are evaporated and the product is purified by passing it over Chelex resin. Absence of free Gd is verified by a test with MTB. Finally the product is lyophilized and is obtained in the form of bright white solid (1.26 g; yield: 99%).

FT-IR (ATR, cm$^{-1}$): 2100 (N$_3$)

MALDI-TOF (dithranol, m/z): 713.16 [M+H$^+$]; 1423.33 [2M+H$^+$] (calculated 713.17 and 1425.34)

% Gd (ICP-MS): 15.4% (calculated 22.09%)

Example 3

Preparation of a P(αPreCL-co-εCL) copolymer 5

Step 1: Synthesis of α-propargyl-ε-caprolactone 4

Synthesis is carried out according to the following reaction scheme:

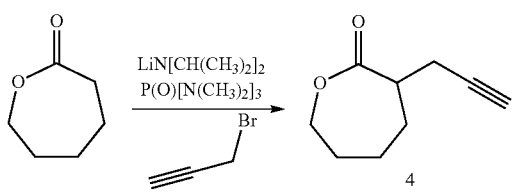

A solution of ε-caprolactone (εCL) (2.5 g; 21.9 mmol) in anhydrous tetrahydrofuran (10 mL) is added dropwise under inert atmosphere to a 2M solution of lithium diisopropyl amide (12 mL; 24.1 mmol) in tetrahydrofuran (80 mL) at −78° C. After one hour at −78° C., propargyl bromide (2.92 mL; 26.3 mmol) and hexamethylphosphoramide (5 mL) are added to lactone enolate. After 3 hours at −30° C., the reaction mixture is neutralized with a solution of ammonium chloride. The product is extracted with dichloromethane (100 mL) and washed with a solution of ammonium chloride and an aqueous solution of sodium chloride. The organic phase is dried over magnesium sulfate, filtered and evaporated at reduced pressure. The product is purified by silica gel column chromatography (heptane/ethyl acetate: 7/3, v/v).

A colorless oil is then obtained (2.01 g, 13.2 mmol, yield: 60%).

$^1$H NMR (300 MHz, CDCl$_3$) δ (ppm)=4.21 (m, 2H, CH$_2$O), 2.73 (m, 1H, COCHCH$_2$), 2.57 (m, 1H, CH$_2$—C≡CH), 2.29 (m, 1H, CH$_2$—C≡CH), 1.99 (m, 2H, CH$_2$CH$_2$O), 1.95 (td, 1H, C≡CH), 1.65 (m, 1H, CH$_2$CH$_2$CH$_2$O), 1.4 (m, 2H, COCHCH$_2$).

$^{13}$C NMR (75 MHz, CDCl$_3$) δ (ppm)=176.2 (C=O), 82.2 (C≡CH), 69.75 (CH$_2$O). 68.81 (C≡CH), 42.60 (COCHCH$_2$), 28.96, 28.89, 28.38, 22.04 (CH$_2$—C≡CH).

IR (ATR, cm$^{-1}$): 3280 (C≡CH), 1720 (C—O).

MS (ES, %): m/z=153.1 (40) [M+H$^+$]; 305.2 (100) [2M$^+$+H].

Step 2: Synthesis of poly(α-propargyl-ε-caprolactone-co-ε-caprolactone) (or (αPreCL-co-εCL) in the bulk 5

Synthesis is carried out according to the following reaction scheme:

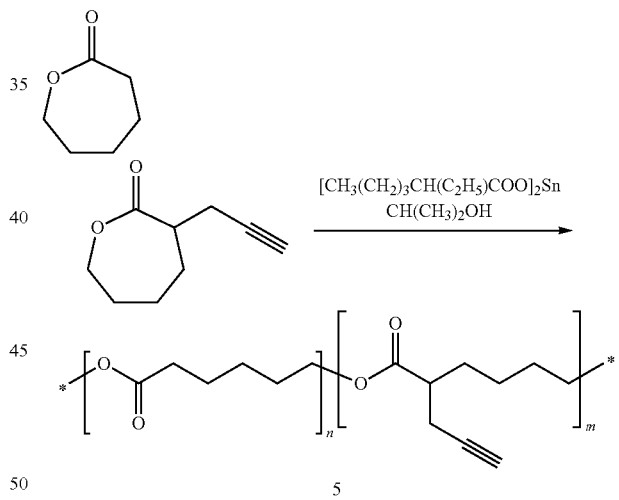

The polymerization reactions were carried out in the bulk, using the conventional Schlenk procedure under inert atmosphere of argon.

Example of Protocol for the Synthesis of P(αPreCL-co-εCL) 10% (i.e. Comprising 10% of Monomer Units Functionalized with a Propargyl Group Relative to the Total Number of Monomer Units):

The εCL (2.66 g, 29.6 mmol, 90 equiv), lactone 4 (0.5 g, 3.29 mmol, 10 equiv), tin octanoate (66.4 mg, 0.164 mol, 0.5 equiv) and isopropanol (25 μL, 0.328 mmol, 1 equiv) are put in a Schlenk. The solution is degassed with three cycles of freezing and thawing. The reaction mixture is stirred under argon for 3.5 h at 140° C. Polymerization is stopped with 1N HCl solution. The polymer is purified by precipitation in methanol, filtered and dried under vacuum to give a white powder.

$^1$H NMR (300 MHz, CDCl3) δ (ppm)=4.96 (m, $(CH_3)_2$CH), 4.02 (t, $CH_2O$), 3.60 (m, $CH_2OH$), 2.50 (m, $COCHCH_2$), 2.26 (t, $COCH_2$), 1.96 (m, C≡CH), 1.49-1.70 (m, $CH_2$—$CH_2$—CH—$CH_2$—O—), 1.29-1.42 (m, $COCH_2CH_2$), 1.18 (d, $(CH_3)_2CH$).

IR (ATR, cm$^{-1}$): 3280 (C≡CH), 1720 (C═O).

The following table shows the variation of the number-average molecular weights and polydispersity index of polymer 5 (determined by CES, in THF medium on PL-gel mixed C columns (Polymer Laboratories)) as a function of the degree of functionalization (determined by proton NMR).

| Degree of functionalization | $M_{n, DRY}$ (g · mol$^{-1}$) | $M_w/M_n$ |
|---|---|---|
| 0% | 37000 | 1.9 |
| 2% | 34000 | 2.3 |
| 5% | 25000 | 1.9 |
| 10% | 18000 | 1.7 |

Example 4

Preparation of the PCL-[Gd(DTPA)] Functionalized Copolymer 6

Synthesis is carried out according to the following reaction scheme:

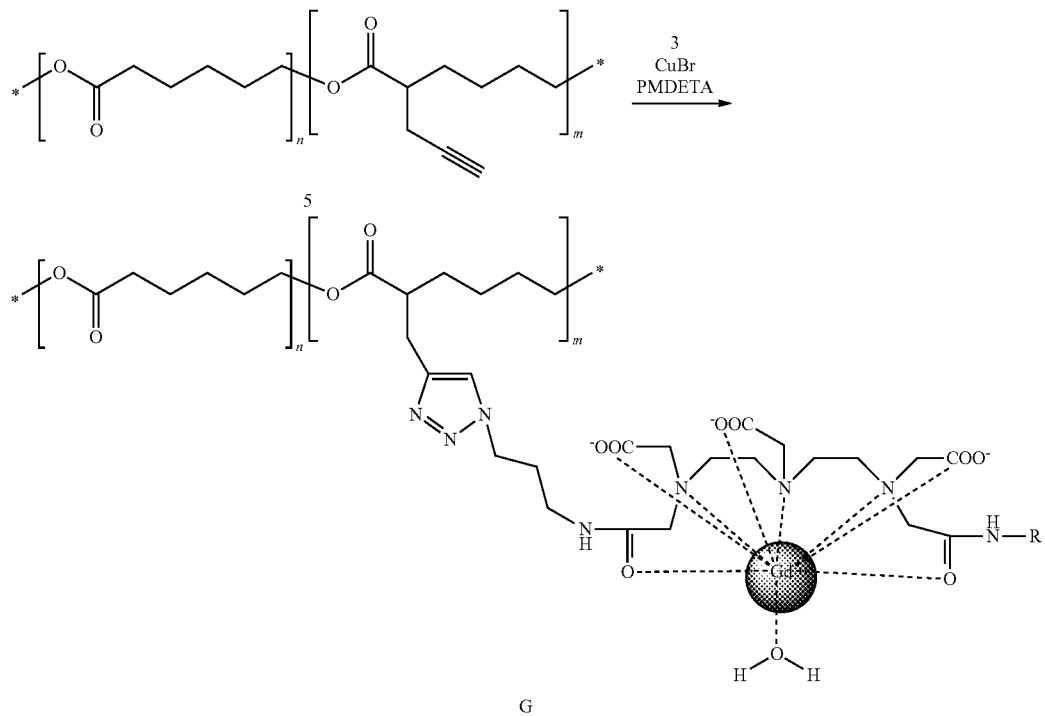

with R+$(CH_2)_3N_3$ 5, complex 3 (3 equiv/unit αPreCL) and CuBr (2 equiv/αPreCL unit) are dissolved in a minimum of DMF. The solution is degassed by three cycles of freezing and thawing. Then pentamethyldiethylenetriamine (PMDETA) (2 equiv/αPrCL unit), previously degassed by bubbling with argon, is added to the medium. The Schlenk is stirred at room temperature for 48 h. The crude reaction product is taken up in THF and dialyzed (pore 3500 g·mol$^{-1}$) against distilled water.

After evaporation of the THF, the polymers are dried under vacuum and analyzed.

Determination of the Percentage by Weight of Gadolinium Per Polymer:

In view of the structure of the [Gd(DTPA-diN$_3$)H$_2$O] complex 3, the latter can react with one or two propargyl functionalized entities of the polymer.

In the following table, the theoretical percentage by weight of gadolinium was calculated on the assumption that each complex reacted with 2 propargyl functionalized entities.

The following table also presents the percentages by weight of gadolinium obtained by elemental analysis by ICP-MS (ICP-MS with quadrupole filter VG Plasmaquad II Turbo and Element XR, samples degraded by a solution of nitric acid and taken up in ultra-pure water, then introduced with a micro-nebulizer at a flow rate of 0.2 ml·min$^{-1}$) as a function of the degree of functionalization of the polymers.

| Nature of the polyester | PCL | PCL-g-[Gd(DTPA)] | | |
|---|---|---|---|---|
| % of initial functionalization (CL-propargyl units) | 0% | 2% | 5% | 10% |

-continued

| Nature of the polyester | PCL | PCL-g-[Gd(DTPA)] | | |
|---|---|---|---|---|
| theoretical wt % of Gd | 0 | 0.910 | 2.097 | 3.712 |
| wt % of Gd measured by ICP-MS | 0 | 1.035 | 2.655 | 3.545 |

Example 5

NMR Experiments

Prior to the experiments on visibility of PCL-[Gd(DTPA)]6 in MRI, $^1$H NMR experiments were carried out in order to estimate the magnitude of the perturbations induced by the gadolinium on the surrounding protons.

In fact, MRI is based on the phenomenon of nuclear magnetic resonance and the abundance of water in the body makes the hydrogen atom the most studied by this technique. The protons subjected to a magnetic field and then to a brief radiofrequency wave are excited and their return to equilibrium or relaxation induces an electromagnetic signal, which after processing gives an MRI image. The image and the contrast are mainly a function of the proton density: p and of the two components of relaxation: longitudinal relaxation (T1) and transverse relaxation (T2).

These 3 parameters are the main ones and they determine the brightness (intensity) of each voxel (volume element investigated) and the contrast (difference in intensity between adjacent voxels).

Gadolinium, like all paramagnetic contrast agents, induces a dipole interaction between its electronic magnetic moment and the nuclear magnetic moment of the nearby protons. It therefore acts indirectly. By shortening the relaxation times T1 and T2 of the tissues in which it is present, gadolinium alters the intensity of their signal. The effect T1 predominates over the effect T2; it is therefore called a T1 contrast agent or positive contrast agent because of the increase in signal that it produces.

The relaxation times of the protons of the various polyesters PCL-[Gd(DTPA)]6 having percentages by weight of gadolinium of 1, 2.6 and 3.5% as well as of the controls PCL and propargyl PCL 5 were measured using $^1$H NMR 400 MHz in an organic medium (DMSO $d_6$).

The samples were prepared at a concentration of 11 mg·mL$^{-1}$ in DMSO. The analyses were carried out at 80° C. Measurement of the relaxation times shows a clear perturbation of the protons of polymer by the complex subjected to the magnetic field. A considerable decrease in the relaxation times (T1) of all the protons is found when gadolinium is present, the more so if the polymer has considerable functionalization.

| proton | δ (ppm) | Relaxation times (ms) | | | | |
|---|---|---|---|---|---|---|
| | | PCL 1 | PCL 2 | PCL 3 | PCL 4 | PCL 5 |
| A | 4.031 | 1554 | 1558 | 536.53 | 273.6 | 252.9 |
| B | 2.284 | 1687 | 1694 | 562.127 | 289.4 | 346.2 |
| C | 1.585 | 1514 | 1505 | 553.936 | 291 | 196.399 |
| D | 1.353 | 1512 | 1502 | 551.918 | 298.991 | 289.2 |

PCL 1: PCL
PCL 2: propargyl PCL 5
PCL 3: PCL-[Gd(DTPA)] 1%
PCL 4: PCL-[Gd(DTPA)] 2.6%
PCL 5: PCL-[Gd(DTPA)] 3.5%

The protons A, B, C and D correspond to the 4 types of protons in PCL. It can be seen that overall, all of the protons are affected by the presence of gadolinium.

Blanquer et al. (WO2011/004332 already cited) imaged polymers in MRI which had relaxation times of around 500 ms, so it can be assumed that the PCLs analyzed comprise percentages by weight of gadolinium that allow imaging by MRI.

An excessively high percentage by weight of gadolinium leads to perturbation such that it becomes difficult to calculate the absolute relaxation times of the protons of the polymers. These values of relaxation times should therefore be used with caution and rather as relative values. Thus, if we construct the curve representing the relative T1 values of the protons of PCL-[Gd(DTPA)], it appears that the decrease in the ratio T1'/T1 (T1 of the protons of PCL-[Gd(DTPA)]/T1 of the protons of PCL) is a nonlinear function of the gadolinium concentration. Now, gadolinium used during MRI examination induces a contrast by decreasing the T1 of the tissues in which it is present. Therefore an increase in signal in MRI of PCL-[Gd(DTPA)] is expected but a priori, starting from a certain amount of gadolinium, the signal will not be better (above a percentage by weight of 2.6%).

FIG. 1 given in the appendix shows the relative variation of the T1 values (T1'/T1) of PCL-[Gd(DTPA)] as a function of the gadolinium concentration.

Example 6

MRI Visualization

The polymers synthesized were submitted to MRI experiments (7T) (imager 7T Bruker DRX300SWB, with a "mini-imagery" configuration gradient 144 mT/m, "birdcage" resonator 30 mm or 64 mm; spin echo sequence 3D) in order to verify the capacity of the PCL-[Gd(DTPA)]prepared for increasing the MRI signal but also to determine the percentages by weight of gadolinium producing optimal visualization in MRI.

Films of about 10 mg containing 30 μg of gadolinium were prepared by mixing unmodified PCLs and PCL-[Gd(DTPA)] containing 1, 2.6 or 3.5% of gadolinium.

The PCLs and PCL-[Gd(DTPA)] were dissolved in a dichloromethane/methanol mixture, before being deposited in molds and dried in order to obtain films.

Sample 2 was obtained by mixing PCL and PCL-[Gd(DTPA)] with a percentage by weight of gadolinium of 1%.

Sample 5 was obtained by mixing PCL and PCL-[Gd(DTPA)] with a percentage by weight of gadolinium of 2.6%.

Sample 8 was obtained by mixing PCL and PCL-[Gd(DTPA)] with a percentage by weight of gadolinium of 3.5%.

Figure 2:
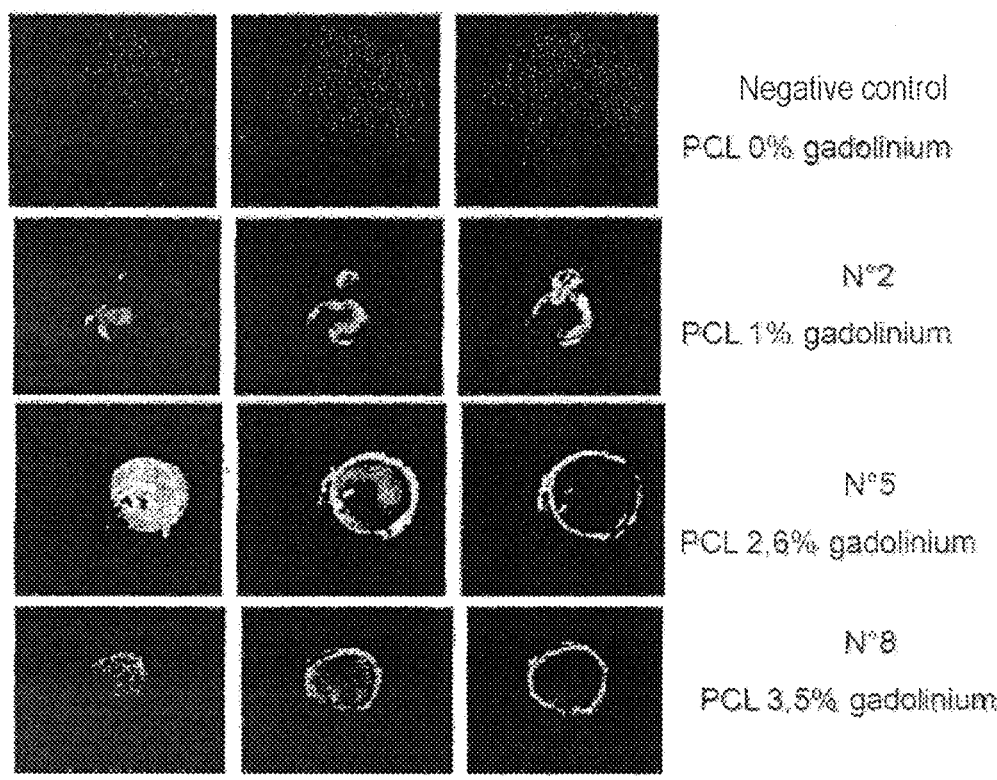
FIG. 2 shows the results obtained in MRI for the three samples 2, 5 and 8 embedded in agarose gels (imager 7T Bruker DRX300SWB, with a "mini-imagery" configuration gradient 144 mT/m, "birdcage" resonator 30 mm or 64 mm; spin echo sequence 3D).

FIG. 2, in the appendix, shows the results obtained in MRI for the three samples 2, 5 and 8 embedded in agarose gels (imager 7T Bruker DRX300SWB, with a "mini-imagery" configuration gradient 144 mT/m, "birdcage" resonator 30 mm or 64 mm; spin echo sequence 3D).

The three images per sample correspond to 3 longitudinal sections of the agarose gel containing the sample.

All the films tested increase the spin-echo signal. However, there is a larger increase in signal for sample 5. These results confirm those obtained in NMR: beyond 2.6% of gadolinium, there is no longer any effect on the proton relaxation time. In MRI, the increase in signal is optimal at this percentage by weight.

Example 7

Preparation of Nanoparticles of PCL-[Gd(DTPA)]6

For preparing nanoparticles of PCL and PCL-[Gd(DTPA)] containing 0.1% of gadolinium, two solutions are prepared:

a solution containing 477.5 mg of PCL, 2.5 mg of PCL-[Gd (DTPA)], 181.2 mg of sorbitan mono-(9Z)-9-octadecenoate (SPAN 80) in 90 mL of acetone, a solution containing 362.3 mg of sorbitan polyoxyethylene (20) monooleate (TWEEN 80) in 181.2 mL of distilled water.

The two solutions are homogenized with magnetic stirring for 3 hours. The first solution is then poured dropwise into the second with magnetic stirring. The mixture is stirred for 3 hours and then the acetone is evaporated under vacuum at room temperature. The solution is then dialyzed for 24 hours against distilled water prior to lyophilization.

Figure 3:
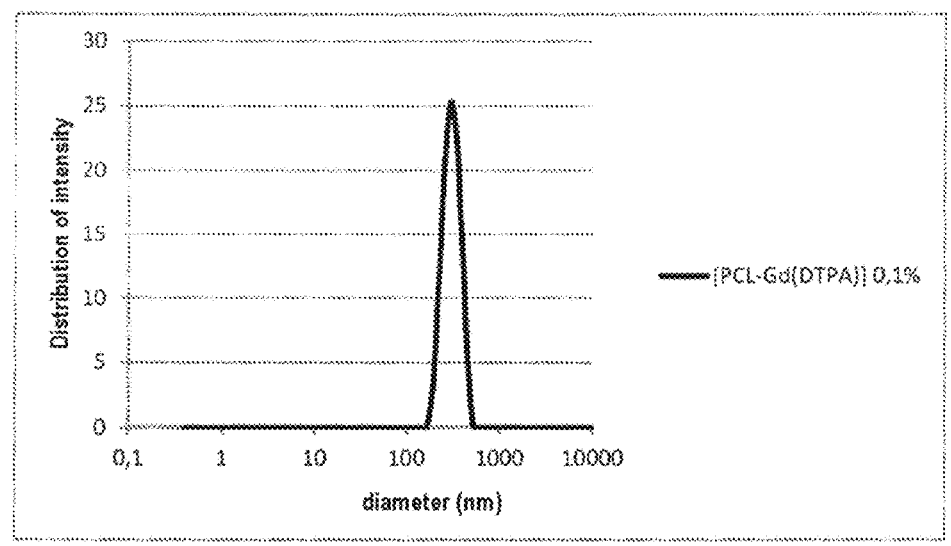
FIG. 3 presents the size distribution of the nanoparticles obtained. The nanoparticles were characterized by DLS analysis on NanoZS apparatus (Malvern) at 25° C. (average diameter of 170 nm).

FIG. 3, in the appendix, presents the size distribution of the nanoparticles obtained. The nanoparticles were characterized by DLS analysis on NanoZS apparatus (Malvern) at 25° C. (average diameter of 170 nm).

Example 8

Visualization of the Nanoparticles of PCL-[Gd(DTPA)]6

The nanoparticles obtained in example 7 were visualized on equipment of the type Imager 7T Bruker BIOSPEC 70/20. The nanoparticles were incorporated in an agarose gel at 1%. The 2D sequence (α=600; TR/TE=110/3.2 ms) was carried out.

Figure 4:
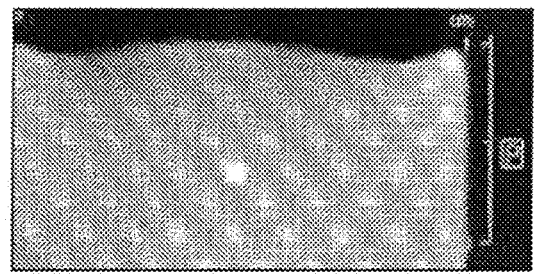
FIG. 4 presents the aggregates of nanoparticles visualized in an agarose gel (gradient echo 2D; α=60° ; TR/TE = 110/3.2 ms.

FIG. 4, in the appendix, presents the aggregates of nanoparticles visualized in an agarose gel (gradient echo 2D; a=60°; TR/TE=110/3.2 ms.

Example 9

Investigation of Stability

Films of PCL and PCL-[Gd(DTPA)]6 are prepared by mixing the various polymers, dissolution in dichloromethane, and then evaporation of the solvent. Mixing is carried out so as to obtain a final gadolinium concentration of 0.4 wt %. Samples of 10 mg are cut from the films obtained and then put in the release medium. In parallel, a film of PCL not containing gadolinium is prepared as negative control.

To evaluate the influence of the presence of proteins and ions present in physiological concentration, which may modify the complexation equilibrium of the gadolinium, the release medium selected contains 3 g of albumin and 0.25 mg of zinc chloride in 75 mL of PBS 1X (phosphate-buffered saline having pH and ionic strengths identical to the physiological medium). Each sample is put in 10 mL of medium and then stirred at 37° C. Aliquots of 1 mL are taken after 1, 3, 7, 15, 30, and 90 days. On taking each sample, the medium containing the films is adjusted to 10 mL with 1 mL of fresh medium to maintain the sink conditions.

These conditions are obtained when the volume of the dissolution medium represents at least from 3 to 10 times the saturation volume. (European Pharmacopeia 7.5 page 721: 5.17.1. Recommendations for the dissolution test)

The release of $Gd^{3+}$ ions is evaluated by ICP-MS analysis. For greater accuracy, an analysis of the release medium is also carried out as second negative control.

Figure 5:
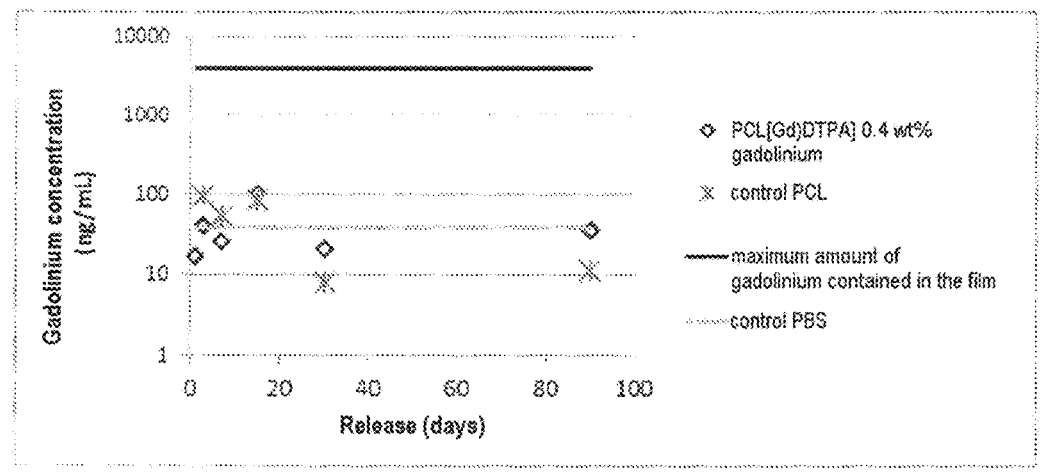
FIG. 5 shows the curve giving the release of gadolinium ions as a function of time for the film of PCL and PCL-[Gd(DTPA)] containing 0.4 wt % of gadolinium. The curve marked PBS control shows the release of gadoliniums ions as a function of time for the film containing the release medium (it is a control).

FIG. 5, in the appendix, shows the curve giving the release of gadolinium ions as a function of time for the film of PCL and PCL-[Gd(DTPA)] containing 0.4 wt % of gadolinium. The curve marked PBS control shows the release of gadolinium ions as a function of time for the film containing the release medium (it is a control).

The diagram in FIG. 5 thus shows that the film containing gadolinium does not release more gadolinium over time than the films not containing it (PCL film and PBS film). Consequently, this film is stable in the release medium.

Example 10

Synthesis of the monomer benzyl 6-oxotetrahydro-2H-pyran-3-ylcarbamate (5-Z-amino-δ-valerolactone=5-NHZ-δ-VL) (9)

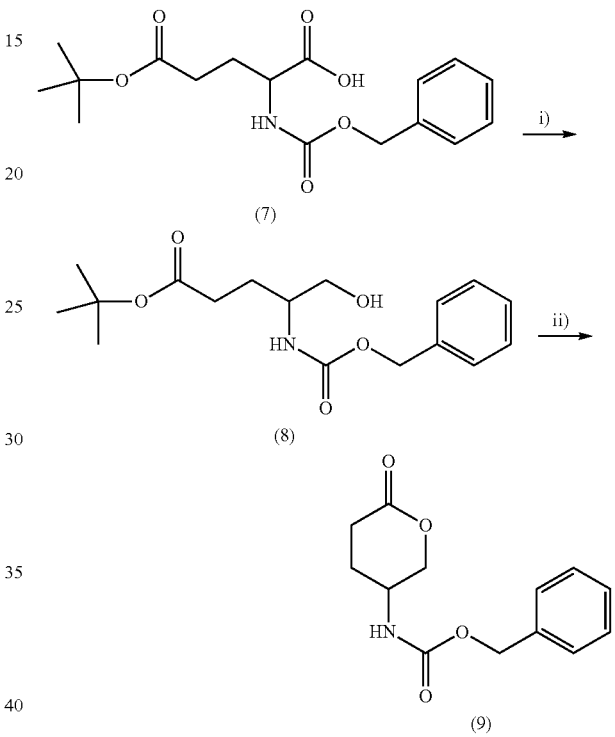

a—Synthesis of tert-butyl-4-(benzyloxycarbonylamino)-5-hydroxypentanoate (8)

Selective reduction of the acid of the main chain of the γ-tert-butyl ester of N-benzyloxycarbonyl-glutamic acid (ZGlu(OtBu)OH) (7) is carried out by formation of an intermediate of the activated ester type by reaction with benzotriazol-1-yloxytris(dimethylamino)phosphonium hexafluorophosphate (BOP). Typically, a solution of N,N-diisopropylethylamine (DIPEA) (1.17 ml, 7.1 mmol) and of 130P (2.87 g, 6.5 mmol) in 10 mL of THF is slowly added to a suspension of 7 (2.02 g, 6 mmol) in 20 mL of THF at room temperature. After stirring for 10 minutes, $Na_3BH_4$ (1.1 g, 30 mmol) is slowly added to the reaction mixture and then reaction is stirred for 2 hours at room temperature. The mixture obtained is diluted in $CH_2Cl_2$ (150 mL) and then washed with a 5% solution of HCl (5×100 mL), followed by washing with saturated solution of $NaHCO_3$ (3×100 mL) and then saturated solution of NaCl (3×100 mL). The organic phase is then dried over $MgSO_4$ and concentrated by evaporation of the solvent, to obtain a clear oil. A final purification is carried out by flash column with $CH_2Cl_2$ as eluent and then ethyl acetate (yield: 90%).

$^1$H-NMR (300 MHz; CDCl$_3$): δ (ppm)=7.3 (m, 5H, Ph), 5.1 (m, 1H, NH), 5.0 (s, 2H, OCH$_2$Ph), 3.8-3.7 (m, 1H, CH—NHZ), 3.6-3.5 (m, 2H, CH$_2$—OH), 2.3-2.2 (m, 2-1, CH$_2$—CH$_2$—CH), 1.9-1.7 (m, 2H, CH$_2$—COOtBu), 1.4 (s, 9H, tBu). HPLC: 1.52 min. Calculated monoisotopic mass (C$_{17}$H$_{25}$NO$_5$) 323.17 g/mol, ES-MS (70 cV, m/z): 324.3 [M+H]$^+$, 346.3 [M+Na]$^+$ b—Synthesis of benzyl 6-oxotetrahydro-2H-pyran-3-ylcarbamate (9)

Lactonization of 8 is carried out in 2 simultaneous steps by elimination of the tert-butyl group and intramolecular cyclization of the intermediate thus formed. Typically, 8 (2 g) is dissolved in a mixture of trifluoroacetic acid (10 mL) and CH$_2$Cl$_2$ (10 mL,) and then stirred for 3 hours at room temperature. After reaction, cold water (80 mL) and CH$_2$Cl$_2$ (80 mL) are added. The organic phase is washed with water (5×50 mL), dried over MgSO$_4$, filtered and then concentrated by evaporation. Purification by column chromatography with EtOAc/Et$_2$O eluent (5:5) gives compound 9 (0.85 g, yield: 55%) in the form of white crystals with a minimum purity of 98%.

T$_m$=65° C. (DSC Perkin Elmer DSC 6000 Thermal Analyzer).

$^1$H NMR (300 MHz; DMSO-d$_6$): δ (ppm)=7.6 (m, 1H, NH), 7.4-7.3 (m, 5H, Ph), 5.05 (s, 2H, OCH$_2$Ph), 4.3-4.2 (m, 1Ha, CH$_2$—O), 4.1-4.0 (m, 1Hb, CH$_2$—O), 3.9-3.8 (m, 1H, CH—NHZ), 2.6-2.4 (m, 2H, CH$_2$—CO), 2.1-2.0 (m, 1Ha, CH$_2$—CH$_2$—CH), 1.8-1.7 (m, 1Hb, CH$_2$—CH—CH).

$^{13}$C NMR (75 MHz, DMSO-d$_6$): δ (ppm)=171 (s, C(O)O), 156.2 (s, NHC(O)O), 137.5 (s, CH$_2$CCH), 128.8-127.6 (m, CH), 70.6 (s, CH$_2$O), 65.9 (s, CH$_2$C(O)ONH), 44.3 (s, CHNH), 27.5 (s, CH$_2$CHNH), 24.5 (s, CH$_2$C(O)). HPLC: 1.23 min.

Calculated monoisotopic mass (C$_{13}$H$_{15}$NO$_4$) 249.10 g/mol, ES-MS (70 eV, m/z): 250.2 [M+H]$^+$, 499.4 [2M+H]$^+$.

Example 11

Synthesis of poly(5-NH$_3^+$-δ-valerolactone-co-ε-caprolactone) (11)

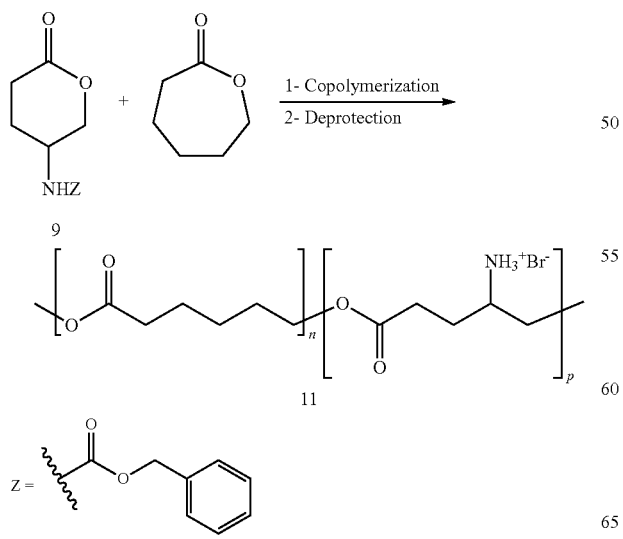

1) Synthesis of poly(5-Z-amino-δ-valerolactone-co-ε-caprolactone) or P(5-NHZ-δ-VL-co-ε-CL) (10)

Typically, 9 (500 mg, 2 mmol) and ε-CL (11.3 mg, 0.10 mmol) are put in a Schlenk under inert atmosphere. The catalyst (Sn(Oct)$_2$, 5 mol %) and the initiator (benzyl alcohol (BzOH), 2.6 M in THF, 0.5 mol %) are added via a septum. The reaction is carried out for 24 hours at 110° C. under inert atmosphere. The reaction is then stopped by adding 3 mL of THF, followed by precipitation in cold methanol. The polymer obtained is filtered and then dried. The comonomer ratios of the copolyester are determined by $^1$H NMR by comparing the intensities of the characteristic signals at 4.95 ppm (s, 2H, OCH$_2$Ph, 9, NHZVL) and 4.00 ppm (t, 2H, OCH$_2$—CH$_2$, ε-CL) and (m, 1Ha, CH$_2$—O, NHZVL). $^1$H NMR (300 MHz; DMSO-d$_6$): δ (ppm)=7.40-7.30 (m, 5H, Ph, NHZVL), 7.20 (m, 1-1H, NH, NHZVL), 4.95 (s, 2H, OCH$_2$Ph, NHZVL), 3.95-4.00 (m, 1Ha, CH$_2$—O, NHZVL and 2H, CH$_2$—O, ε-CL), 3.85 (m, 1Hb, CH$_2$—O, NHZVL), 3.65 (m, 1H, CH—NHZ, NHZVL), 2.2-2.3 (m, 2H, CH$_2$—CO, NHZVL and 2H, CH$_2$—CO, ε-CL), 1.65 (m, 1Ha, CH$_2$—CH$_2$—CH, NHZVL), 1.50 (m, 1Hb, CH$_2$—CH$_2$—CH, NHZVL and 4H, CH—CH$_2$—CH$_2$, ε-CL), 1.30 (m, 2H, —CH$_2$—CH$_2$—CH$_2$, ε-CL).

2) Synthesis of poly(5-NH$_3^+$-δ-valerolactone-co-ε-caprolactone) or P(5-NH$_3$-δ-VL-co-ε-CL)(11)

The amine functions are deprotected in an acid medium to generate the corresponding polymer bearing ammonium pendant groups. Typically, a solution of hydrobromic acid (3 eq. per protective group) in acetic acid (33 wt %) is added slowly with stirring to a suspension of copolymer to be deprotected (10% w:v) in dichloromethane. Deprotection is carried out at room temperature and then stopped after 20 minutes. The reaction mixture is precipitated and then washed with diethyl ether and water to remove the excess salts.

$^1$H NMR: (300 MHz; DMSO-d$_6$): δ (ppm)=4.20 (m, 1Ha, CH$_2$—O, NH$_3$VL), 4.10 (m, 1Hb, CH$_2$—O, NH$_3^+$VL), 4.00 (2H, CH$_2$—O, ε-CL), 3.5 (m, 1H, CH—NH$_3$, NH$_3^+$VL), 2.60 (m, 2H, CH$_2$—CO, NH$_3^+$VL), 2.30 (m, 2H, CH$_2$—CO, ε-CL), 1.90 (m, 2H, CH$_2$—CH$_2$—CH, NH$_3^+$VL), 1.55 (m, 4H, CH$_2$—CH$_2$—CH$_2$, ε-CL), 1.30 (m, 2H, —CH$_2$—CH$_2$—CH$_2$, ε-CL).

Example 12

Synthesis of poly(5-DTPA-6-valerolactone-co-ε-caprolactone) (P(DTPA-VL-co-CL)) (12)

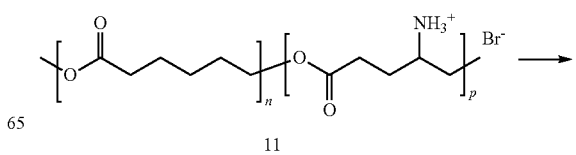

-continued

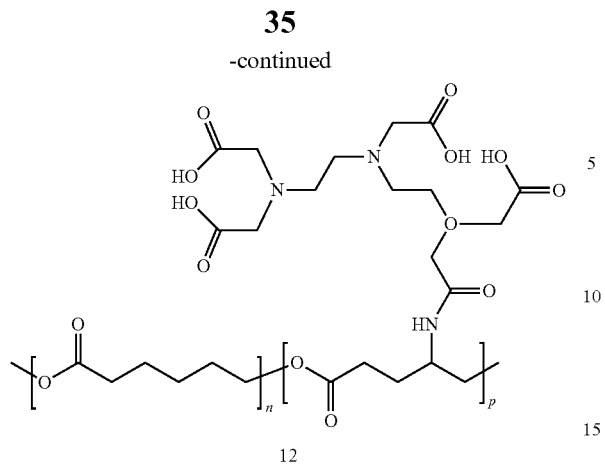

12

DTPA dianhydride (5 mg; $4.14\times10^{-3}$ mol) dissolved beforehand in anhydrous DMF (3 mL) is added dropwise to a solution of P(5-$NH_3^+$-δ-VL-co-ε-CL) 11 (25 mg; $1.05\times10^{-5}$ mol) in anhydrous DMF (4 mL) in the presence of triethylamine (6 μL; $3.17\times10^{-5}$ mol). The reaction mixture is stirred at room temperature for 24 hours. After evaporating the DMF, the polymer is precipitated in methanol and dried before analysis.

Figure 6:
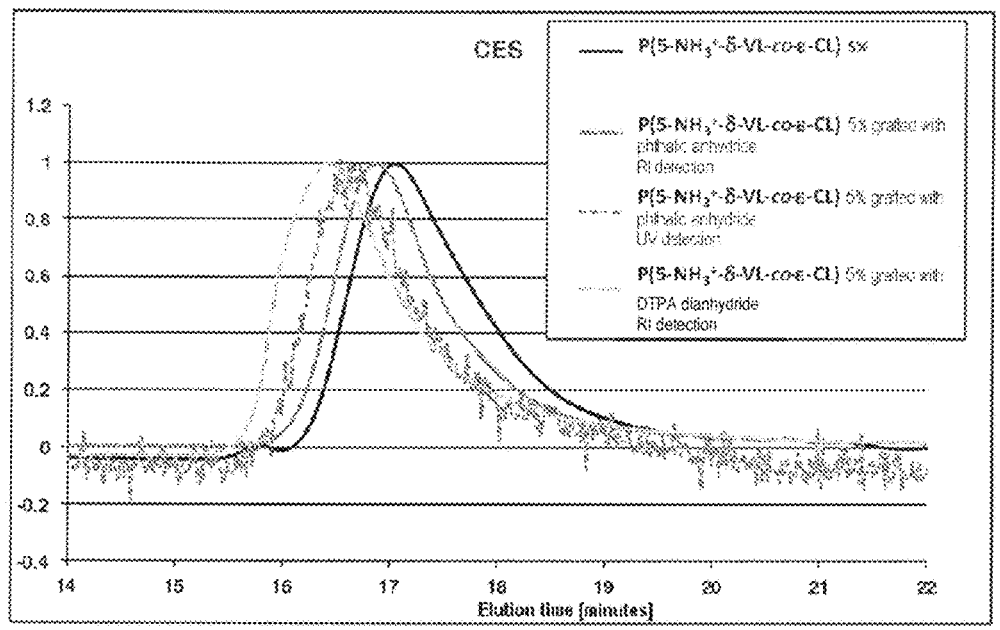
FIG. 6 shows the graphs obtained from the analyses by size exclusion chromatography.

The superimposed chromatograms (CES, THF, refractometric and UV double detection) of polymers 11, 12 and of polymer 11 coupled to a phthalic anhydride (UV marker) confirm grafting of DTPA on the copolymer (FIG. 6 in the appendix shows the graphs obtained from the analyses by size exclusion chromatography).

The degree of functionalization determined by $^1$H NMR is 5%. In contrast to example 4, each DTPA dianhydride reacts here with a single amine group to form an amide bond.

Example 13

Complexation of Gadolinium with 12

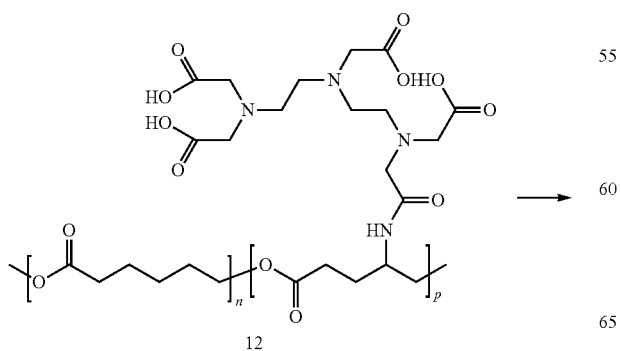

12

-continued

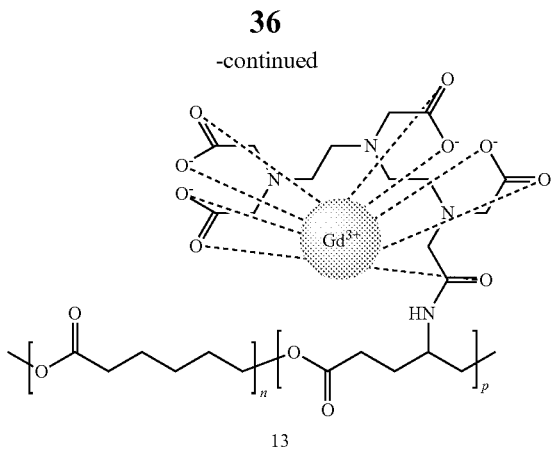

13

Copolymer 12 (30 mg; $1.15\times10^{-5}$ mol) is dissolved in a minimum of DMSO (5 mL). $GdCl_3$-$6H_2O$ (8.4 mg; $2.5\times10^{-5}$ mol) is then added to the medium. After 4 days, with stirring at room temperature, the complexed polymer is purified by dialysis against methanol.

Percentage by weight of gadolinium of 13 measured by ICP-MS: 2%

Percentage by weight of gadolinium calculated as percentage of gadolinium relative to the expected empirical formula: 5.7%

Example 14

Visibility of P[Gd(DTPA)/VL-co-CL] 13

A film of PCL and P[Gd(DTPA)/VL-co-CL] 13 was prepared by mixing the various polymers, dissolution in dichloromethane, and then solvent evaporation. Mixing is carried out so as to obtain a final gadolinium concentration of 1 wt %. Visualization of the film was carried out on apparatus of the type Imager 7T Bruker BIOSPEC 70/20 on films incorporated in agarose gel at 1%. The sequences 2D (α=600; TR/TE=110/3.2 ms), and echo 3D of echo gradient (three weightings α=75°, 30° and 15°) and RARE (Rapid Acquisition with Relaxation Enhancement) were carried out.

Figure 7:
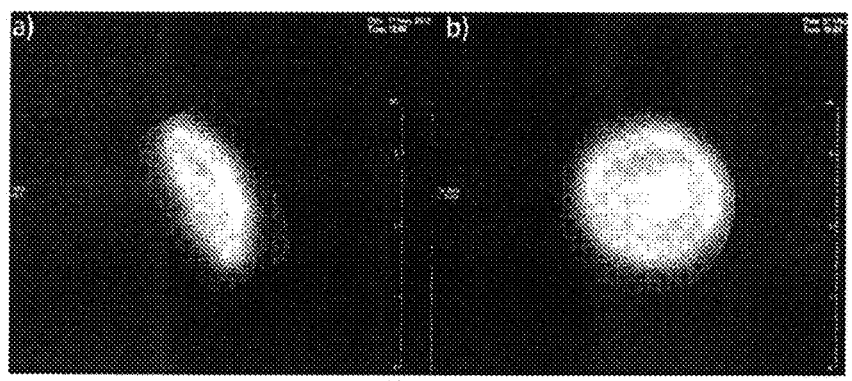
FIG. 7 shows two plates (a and b) obtained from 3D reconstruction of the images.

FIG. 7 in the appendix shows two plates (a and b) obtained from 3D reconstruction of the images.

Figure 8:
FIG. 8 shows that the object visualized is in the form of a dish, which corresponds to the shape of the mold.

FIG. 8 in the appendix shows that the object visualized is in the form of a dish, which corresponds to the shape of the mold. This proves that PCL and P[Gd(DTPA)/VL-co-CL] are soluble in dichloromethane, since the object visualized took the shape of the mold. This experiment shows the advantage of using thermoplastic polymers in the present invention. In fact their solubility in hydrophobic solvents makes it possible to coat an object by simple dissolution in a solvent followed by evaporation of the solvent.

Example 15

Synthesis of Poly(Methyl Acrylate-Co-Propargyl Acrylate)

a—Preparation of Copolymer P(MA-Co-PA) 5% (i.e. Comprising 5% of Acrylate Monomer Units Functionalized with a Propargyl Group Relative to the Total Number of Acrylate Monomer Units)

Methyl acrylate MA (5 g, 58.1 mmol, 95 equiv), propargyl acrylate PA (0.337 g, 3.06 mmol, 5 equiv), AIBN (10 mg, $64.9\times10^{-3}$ mmol, 0.2% wt) and toluene (20 mL) are put in a Schlenk. The solution is degassed by three cycles of freezing and thawing. The reaction mixture is stirred under argon for 4 hours at 65° C. The polymer is purified by precipitation in heptane, filtered and dried under vacuum to give a colorless solid.

$^1$H NMR (300 MHz, CDCl3) δ (ppm)=4.60 (O—CH$_2$—C≡CH), 3.59 (O—CH$_3$), 1.91 (O—CH$_2$—C≡CH), 2-0.5 (CH$_2$—CH)

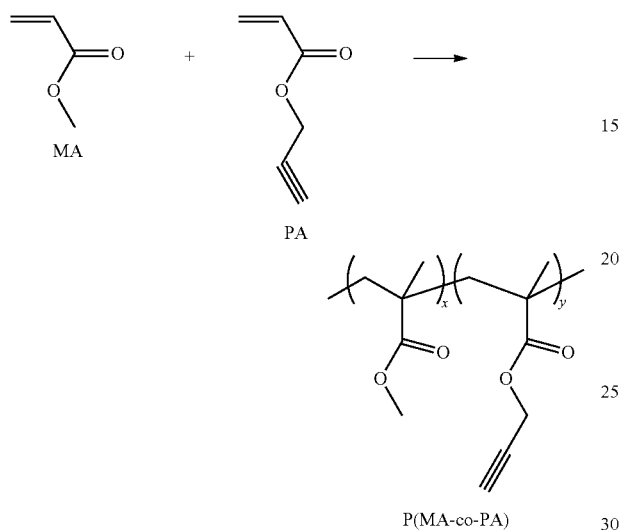

P(MA-co-PA)

b—Synthesis of the Functionalized Poly(Methyl Acrylate) P(MA-Co-PA)-[Gd(DTPA)]

Copolymer P(MA-co-PA) at 5%, complex 3 (3 equiv/propargyl acrylate monomer unit), CuBr (2 equiv/propargyl acrylate monomer unit), and a minimum of DMF are added to a Schlenk tube equipped with a magnetized bar. The solution is degassed by three cycles of freezing and thawing. Then pentamethyldiethylenetriamine (PMDETA) (2 equiv/propargyl acrylate monomer unit), previously degassed by bubbling with argon, is added to the reaction mixture. The Schlenk is stirred at room temperature for 48 hours. The crude reaction product is taken up in THF and dialyzed (pore 6000-8000 g·mol$^{-1}$) against distilled water.

After evaporation of the solvent, the polymers are dried under vacuum and analyzed.

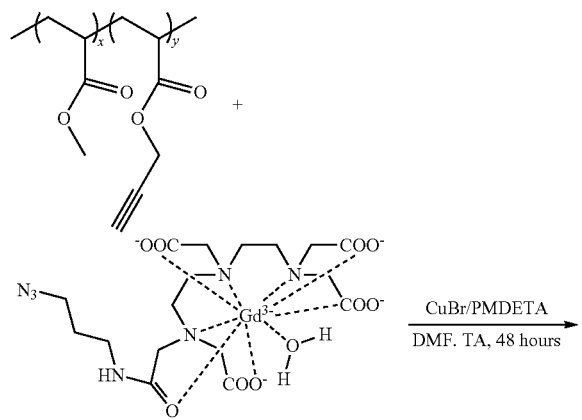

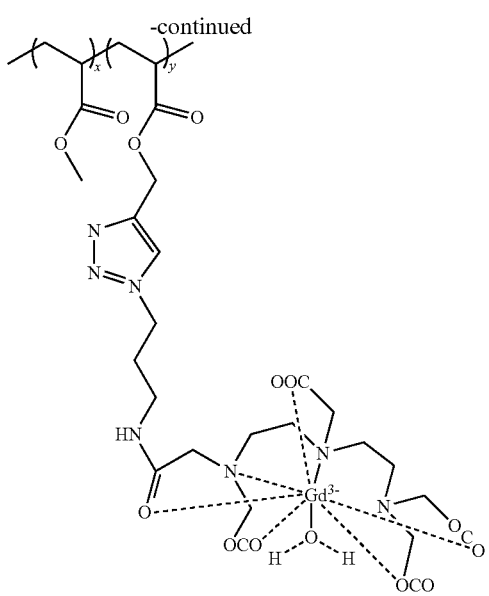

The invention claimed is:

1. A hydrophobic thermoplastic copolymer, comprising:
   a first monomer unit, and
   a second monomer unit on which is grafted a paramagnetic-ion-chelating ligand that optionally complexes with a paramagnetic ion or a paramagnetic-ion-chelating ligand complexed with the paramagneticion,
   wherein the second monomer unit is grafted in sufficient amount for the copolymer to be visible in magnetic resonance imaging when the second monomer unit is complexed with the paramagneticion,
   wherein the copolymer has a degree of functionalization of from 0.01 to less than 10%,
   wherein the copolymer is obtained by copolymerization of the first monomer unit and the second monomer unit,
   wherein the grafting is provided by amidation, esterification or click chemistry and, said click chemistry giving a linkage function selected from the group consisting of triazole, tetrazole, carbamate, urea, thioether, ether, oxime and thiocarbamate and
   wherein the copolymer, when the grafting is provided by click chemistry and gives a triazole linkage, is obtained from one selected from the group consisting of: a random copolymer of caprolactone (CL) and propargyl caprolactone (CL-propargyl or Pr-CL), a block copolymer of caprolactone (CL) and propargyl caprolactone (CL-propargyl or Pr-CL), a random copolymer of caprolactone (CL) and 5-NH3 +-δ-valerolactone (5-NH3 +-δ-VL), a block copolymer of caprolactone (CL) and 5-NH3 +-δ-valerolactone (5-NH3 +-δ-VL) and a copolymer of polymethyl acrylate or polymethylmethacrylate and propargyl acrylate.

2. The copolymer of claim 1, wherein the first monomer unit is a monomer for preparing biostable homopolymers.

3. The copolymer of claim 1, wherein the second monomer unit is functionalized with an azide, alkyne, carboxylic acid, ester, anhydride, acid halide, amide, iso(thio)cyanate, epoxide, thiol, amine, ketone, diene, alkene, or hydroxyl function, protected or unprotected.

4. The copolymer of claim 1, further comprising: at least one additional block selected from the group consisting of poly(ethylene glycol), poly(propylene glycol) and poloxamer.

5. The copolymer of claim 1, which is bioabsorbable.

6. The copolymer of claim 1, wherein a complex of the paramagnetic ion comprises a chelating ligand comprising a carboxylic acid function.

7. A method of preparing the copolymer of claim 1, the method comprising:
   (i) preparing, by copolymerization, a copolymer comprising the first monomer unit and the second monomer unit, and
   (ii) grafting, onto the second monomer unit, the complex of the paramagnetic ion or the paramagnetic-ion-chelating ligand that optionally complexes with the paramagnetic ion by amidation, esterification or click chemistryand , said click chemistry giving a linkage function selected from the group consisting of triazole, tetrazole, carbamate, urea, thioether, ether, oxime and thiocarbamate and
   wherein the copolymer, when the grafting is provided by click chemistry and gives a triazole linkage, is obtained from one selected from the group consisting of: a random copolymer of caprolactone (CL) and propargyl caprolactone (CL-propargyl or Pr-CL), a block copolymer of caprolactone (CL) and propargyl caprolactone (CL-propargyl or Pr-CL), a random copolymer of caprolactone (CL) and 5-NH3 +-δ-valerolactone (5-NH3 +-δ-VL), a block copolymer of caprolactone (CL) and 5-NH3 +-δ-valerolactone (5-NH3 +-δ-VL) and a copolymer of polymethyl acrylate or polymethylmethacrylate and propargyl acrylate.

8. A medical device, comprising:
   the copolymer of claim 1 in bulk and/or as a coating and/or as marking, wherein the medical device is detectable in magnetic resonance imaging.

9. A method of preparing a medical device detectable in magnetic resonance imaging, the method comprising:
   coating the medical device with a solution comprising the copolymer of claim 1.

10. A method of marking a medical device, the method comprising:
    depositing the copolymer of claim 1 on a surface of the medical device.

11. The copolymer of claim 1, wherein the first monomer unit is selected from the group consisting of
    a monomer for preparing a polyolefin,
    a monomer for preparing a fluoro polymer,
    a monomer for preparing a semi-aromatic polyester,
    a monomer for preparing a polyurethane, and
    a monomer for preparing a silicone.

12. The copolymer of claim 1, wherein the first monomer unit is selected from the group consisting of an aliphatic polyester, poly(1,4-dioxane-2,3-diones) and poly(para-dioxanones).

* * * * *